(12) United States Patent
Milanovich

(10) Patent No.: US 7,930,190 B1
(45) Date of Patent: Apr. 19, 2011

(54) METHODS OF RATING SERVICE PROVIDERS

(76) Inventor: Philip John Milanovich, Phoenix, AZ (US)

( * ) Notice: Subject to any disclaimer, the term of this patent is extended or adjusted under 35 U.S.C. 154(b) by 865 days.

(21) Appl. No.: 11/775,232

(22) Filed: Jul. 10, 2007

Related U.S. Application Data

(63) Continuation-in-part of application No. 10/249,270, filed on Mar. 27, 2003, now Pat. No. 7,346,525, and a continuation-in-part of application No. 10/882,262, filed on Jul. 2, 2004, now abandoned.

(51) Int. Cl.
*G06Q 10/00* (2006.01)

(52) U.S. Cl. .......................................................... 705/2

(58) Field of Classification Search ................... 705/2, 3
See application file for complete search history.

(56) References Cited

U.S. PATENT DOCUMENTS

| | | | |
|---|---|---|---|
| 5,752,237 | A | 5/1998 | Cherney |
| 5,845,254 | A | 12/1998 | Lockwood et al. |
| 5,852,808 | A | 12/1998 | Cherney |
| 5,999,909 | A | 12/1999 | Rakshit et al. |
| 6,128,620 | A | 10/2000 | Pissanos et al. |
| 6,223,164 | B1 | 4/2001 | Seare et al. |
| 6,272,471 | B1 | 8/2001 | Segal |
| 6,317,719 | B1 | 11/2001 | Schrier et al. |
| 6,394,811 | B2 | 5/2002 | Finitzo et al. |
| 2002/0029157 | A1 | 3/2002 | Marchosky |
| 2002/0082876 | A1 | 6/2002 | Martin et al. |
| 2002/0087354 | A1 | 7/2002 | Martin et al. |
| 2002/0194033 | A1 | 12/2002 | Huff |
| 2003/0009359 | A1 | 1/2003 | Weidner et al. |
| 2003/0028406 | A1 | 2/2003 | Herz et al. |
| 2003/0167187 | A1 * | 9/2003 | Bua ................................... 705/2 |
| 2004/0267579 | A1 | 12/2004 | Markman |
| 2007/0136091 | A1 * | 6/2007 | McTaggart ....................... 705/2 |
| 2007/0214013 | A1 * | 9/2007 | Silverman ......................... 705/2 |

FOREIGN PATENT DOCUMENTS

| | | |
|---|---|---|
| JP | 57-34265 | 2/1982 |
| JP | 2002-132955 | 5/2002 |

OTHER PUBLICATIONS

Norm Andrzejewski and Rosalinda T. Lagua, Use of a Customer Satisfaction Survey by Health Care Regulators, Public Health Reports, vol. 112, pp. 206-210, May-Jun. 1997.
Patrick et al., Are Hospital Characteristics Associated with Parental Views of Pediatric Inpatient Care Quality?, American Academy of Pediatrics, Pediatrics, vol. 111, pp. 308-314, Feb. 2003.

* cited by examiner

*Primary Examiner* — Gerald J. O'Connor
*Assistant Examiner* — Edward Winston
(74) *Attorney, Agent, or Firm* — Swift Law Office; Stephen Christopher Swift

(57) ABSTRACT

A method of providing insurance (including professional malpractice liability insurance) to consumers against unfavorable outcomes resulting from services, methods of rating risks associated with services, and a method of reducing the risk of unfavorable outcomes. In the first preferred embodiment, a policy limit is chosen by a patient (or other consumer), a premium based on the policy limit is paid by the patient, and if malpractice is committed by a health care provider (or other professional), the consumer is compensated up to the amount of the policy limit. The consumer signs an agreement that the liability of the service provider for malpractice will not exceed the policy limit. Risk factors are evaluated for the consumer, the doctor, hospital or other service provider, and the procedures that are to be performed, and are used to determine the amount of the premium, taking into account the policy limit chosen by the consumer.

5 Claims, 22 Drawing Sheets

METHODS OF RATING SERVICE PROVIDERS

CROSS REFERENCE TO RELATED APPLICATIONS

This application is a Continuation-In-Part of Utility patent application Ser. No. 10/249,270, filed Mar. 27, 2003, and a Continuation-In-Part of Utility patent application Ser. No. 10/882,262, filed Jul. 2, 2004, both of which are incorporated herein by reference.

BACKGROUND OF THE INVENTION

1. Field of the Invention

The present invention relates to insurance (including professional malpractice liability insurance) to consumers against unfavorable outcomes resulting from services, methods of rating risks associated with the services, and methods of reducing the risk of unfavorable outcomes.

2. Description of the Prior Art

The United States of America is currently facing a crisis relating to liability for medical malpractice and insurance for it. It is difficult or impossible for many physicians to pay the premiums required for adequate professional liability coverage. However, the "caps" on liability for punitive damages, that have already been enacted in some states, and are proposed in other states and at the federal level in Congress, are likely to deprive victims of adequate compensation. E.g., a young person, who is severely injured as a result of medical malpractice, may not be able to hold a normal job, and thus may be impoverished under the proposed caps, because the maximum compensation allowed under the proposed reforms may be grossly inadequate to compensate for a young person's pain and suffering over a lifetime. There have been a number of prior patents relating to professional malpractice and methods for reducing the cost of insurance.

U.S. Pat. No. 5,752,237, issued on May 12, 1998, to Julius Cherny, discloses a method and apparatus for providing professional liability coverage to professionals such as lawyers and accountants having large numbers of publicly traded corporate clients. It would allow the professionals or their insurance companies to sell short the stock of corporations when the price of, their stock goes down due to professional malpractice. This would reduce the premiums paid by the insured professionals and/or increase the profits of the insurance companies.

U.S. Pat. No. 5,845,254, issued on Dec. 1, 1998, to Edward J. Lockwood, Jeffrey Tarrant and Michael Volpe, discloses a method and apparatus for objectively monitoring and assessing the performance of health-care providers based on the severity of sickness episodes treated by the providers. The rating method of the present invention is distinguishable, in that it uses other factors besides the severity of sickness episodes to rate health-care providers.

U.S. Pat. No. 5,852,808, issued on Dec. 22, 1998, to Julius Cherny, discloses the same method and apparatus for providing professional liability coverage as the previous patent, but has different claims.

U.S. Pat. No. 5,999,909, issued on Dec. 7, 1999, to Amitabha Rakshit and Wilson A. Judd, discloses a method for establishing certifiable patient informed consent for a medical procedure. Like the present invention, it uses software to reduce medical malpractice costs.

U.S. Pat. No. 6,128,620, issued on Oct. 3, 2000, to Patricia L. Pissanos and Stephen M. Beasley, discloses a database for compiling information for medical malpractice litigation.

U.S. Pat. No. 6,223,164, issued on Apr. 24, 2001, to Jerry G. Seare et al., discloses a method and system for generating statistically-based medical provider utilization profiles. The profiles can then be used for comparison of a medical provider to a normative profile. The rating method of the present invention is distinguishable, in that it uses other factors to determine the risk of an unfavorable outcome.

U.S. Pat. No. 6,272,471, issued on Aug. 7, 2001, to Jeffrey J. Segal, discloses a method and apparatus for deterring frivolous professional liability claims, by paying the legal costs of countersuits for improper prosecution when a frivolous claim has been made.

U.S. Pat. No. 6,317,719, issued on Nov. 13, 2001, to Robert W. Schrier et al., discloses systems and methods for providing patient-specific drug information, designed for use by doctors. The information system of the present invention is distinguishable, in that it provides information directly to patients.

U.S. Pat. No. 6,394,811, issued on May 28, 2002, to Terese Finitzo and Kenneth D. Pool, Jr., discloses computer-automated implementation of user-definable decision rules for medical diagnostic or screening interpretations. The information system of the present invention is distinguishable, in that it provides information directly to patients, and is not designed as substitute for the doctor's judgment.

U.S. Patent Application Publication No. 2002/0029157, published on Mar. 7, 2002, to J. Alexander Marchosky, discloses a patient-controlled automated medical record, diagnosis, and treatment system and method. The information system of the present invention is distinguishable, in that it provides information to doctors and other providers, as well as patients, and it is related to insurance against malpractice and other unfavorable outcomes.

U.S. Patent Application Publication No. 2002/0082876, published on Jun. 27, 2002, by David A. Martin and David R. Montgomery, discloses a process for linking credentialing information with a medical malpractice insurance application. U.S. Patent Application Publication No. 2002/0087354, published on Jul. 4, 2002, by David A. Martin and David R. Montgomery, discloses the same process, with additional claims. Neither disclose the method of rating service providers of the present invention.

U.S. Patent Application Publication No. 2002/0194033, published on Dec. 19, 2002, by David S. Huff, discloses a method and system for automatically extracting data and generating insurance quotes, including the preparation and use of risk information profiles on clients. The present invention is distinguishable, in that it also includes the preparation and use of risk factors for service providers.

U.S. Patent Application Publication No. 2003/0009395, published on Jan. 9, 2003, by James Weidner, David Preimesberger and A. Peter Kezirian, Jr., discloses property/casualty insurance entities and techniques, which remove unlimited liability and cap annual assessments, while retaining the lower cost achievable by claims-paid policy.

U.S. Patent Application Publication No. 2003/0028406, published on Feb. 6, 2003, by Frederick S. M. Herz and Walter Paul Labys, discloses a database for screening potentially litigious patients.

U.S. Patent Application Publication No. 2004/0267579, published on Dec. 30, 2004, by Barry S. Markman, discloses a method, apparatus and system for providing insurance coverage and claims payment for single event surgical and diagnostic procedures, but does not disclose the method of rating hospitals and other service providers of the present invention.

Japanese Patent No. 57-34265, published on Feb. 24, 1982, inventor Yoshikuni Tazawa et al., discloses a medical business system related to insurance.

Japanese Patent No. 2002-132955, published on May 10, 2002, inventor Takayuki Saito, discloses a system for reducing and preventing medical malpractice.

Norm Andrzejewski and Rosalinda T. Lagua, Use of a Customer Satisfaction Survey by Health Care Regulators: A Tool for Total Quality Management, 1997 U.S. Department of Health and Human Services; Public Health Reports, Public Health Report 1997; vol. 112, pp. 206-210, May-June 1997, discloses the use of a survey to determine quality of service, but does not disclose the method of rating hospitals and other service providers of the present invention.

Patrick et al., Are Hospital Characteristics Associated with Parental Views of Pediatric Inpatient Care Quality?, American Academy of Pediatrics, Pediatrics, vol. 111, pp. 308-14, February 2003, discloses the use of hospital characteristics to access quality, but does not disclose the method of rating hospitals and other service providers of the present invention.

None of the above inventions and patents, taken either singly or in combination, is seen to describe the present invention as claimed.

SUMMARY OF THE INVENTION

The present invention is a method and system of providing insurance (including professional malpractice liability insurance) to consumers against unfavorable outcomes resulting from services, methods of rating risks associated with the services based on objective factors, a method of reducing the risk of unfavorable outcomes, and a method and system of providing insurance, including medical health insurance, on an individual-cost-specific basis, rather than a group-cost-specific basis. The first preferred embodiment is a method and system of providing professional liability insurance, with premiums pre-paid by consumers. A policy limit is chosen by a patient (or other consumer), a premium based on the policy limit is paid by the patient, and if malpractice is committed by a health care provider (or other professional), the patient is compensated up to the amount of the policy limit. The patient signs an agreement that the liability of the health care provider for malpractice will not exceed the policy limit. Only then are medical services provided. Risk factors are developed and evaluated for the patient, the doctor, hospital or other health care provider, and the procedures that are to be performed, and are used to determine the amount of the premium, taking into account the policy limit chosen by the patient. The total cost of the premium for insurance with insurance with a given policy limit will be a function of the probability of an unsuccessful diagnosis and/or procedure for a given patient, hospital and/or doctor times the cost associated with the result on non-success.

The second preferred embodiment is the same as the first preferred embodiment, except that what is insured against is not only malpractice, but compensation is provided to the consumer for any unfavorable outcome of the services. The third preferred embodiment is the same as the first preferred embodiment, except that the premium is paid by the doctor or other service provider. The fourth preferred embodiment is the same as the second preferred embodiment, except that the premium is paid by the service provider. The fifth preferred embodiment is the system of rating risks by itself, and the data bases that are created and maintained in the system, which may be used independently of the insurance system.

The sixth preferred embodiment is a method of rating hospitals for their risk of medical malpractice liability. The seventh preferred embodiment is a method of reducing the risk of malpractice or other unfavorable outcomes. The eighth preferred embodiment is a method of rating a service provider for risk of malpractice or other unfavorable outcomes.

The ninth preferred embodiment is an alternative method of providing medical malpractice insurance, which is an adaptation and modification of the first preferred embodiment. The tenth preferred embodiment is a method of drug cost analysis. The eleventh preferred embodiment is a method of providing health care insurance on an individual basis rather than a group basis.

The medical malpractice insurance that is included within the scope of the present invention is like the prior art flight insurance that a consumer bought before getting on an airplane, in that if he (or she) does not buy the insurance the consumer does not get on the flight or see the doctor. It differs in that the provider (i.e., airline or doctor) could pay for, the policy. The insurance company and/or anyone else could also pay for the policy, but the beneficiary must be the consumer (i.e., the patient or passenger).

Accordingly, it is a first object of the invention to provide a solution to the medical malpractice insurance crisis.

It is a second object of the invention to provide an alternative system for providing medical malpractice insurance, that insures adequate compensation to injured patients, but will not bankrupt doctors or their insurance carriers.

It is a third object of the invention to provide a system of malpractice insurance that gives freedom of choice to consumers.

A fourth object of the invention is to provide a system of malpractice insurance that may be adapted to any profession needing professional liability insurance.

A fifth object of the invention is to provide a system of insuring consumers against unfavorable outcomes resulting from services.

A sixth object of the invention is to provide systems for rating risks based on objective factors, that is event specific, in that the risk rating is determined at the point of contact for a particular event.

A seventh object of the invention is to provide a method for reducing the risk of malpractice and other unfavorable outcomes.

An eighth object of the invention is to provide an individual rather than group based concept for malpractice insurance.

A ninth object of the invention is to provide a system that enables patients to be proactive rather than merely reactive in the medical malpractice process.

A tenth object of the invention is to provide cost coverage that is individual and event specific, rather than group specific with no consideration of the individual.

An eleventh object of the invention is to provide a system of compensation in which the amount received is point and event specific.

A twelfth object of the invention is to provide a system of compensation that reduces the need for litigation.

A thirteenth object of the invention is to provide a system of compensation that enables both consumers and service providers t be proactive rather than merely reactive.

A fourteenth object of the invention is to provide a system of compensation that educates patients, by providing them with information about what they are being treated for and how they are being treated.

These and other objects of the present invention will become readily apparent upon further review of the following specification and drawings.

DETAILED DESCRIPTION OF THE PREFERRED EMBODIMENTS

The present invention is a method for providing insurance to consumers against unfavorable outcomes resulting from services, methods of rating risks associated with the services based on objective factors, and a method of reducing the risk of unfavorable outcomes.

The first preferred embodiment of the invention is a system for providing professional malpractice liability insurance, in which the premiums are pre-paid by the consumers. It is designed primarily for medical malpractice liability insurance, but may also be applied to malpractice liability insurance for other professions, such as dentists, lawyers, accountants or stockbrokers.

Figure 1:
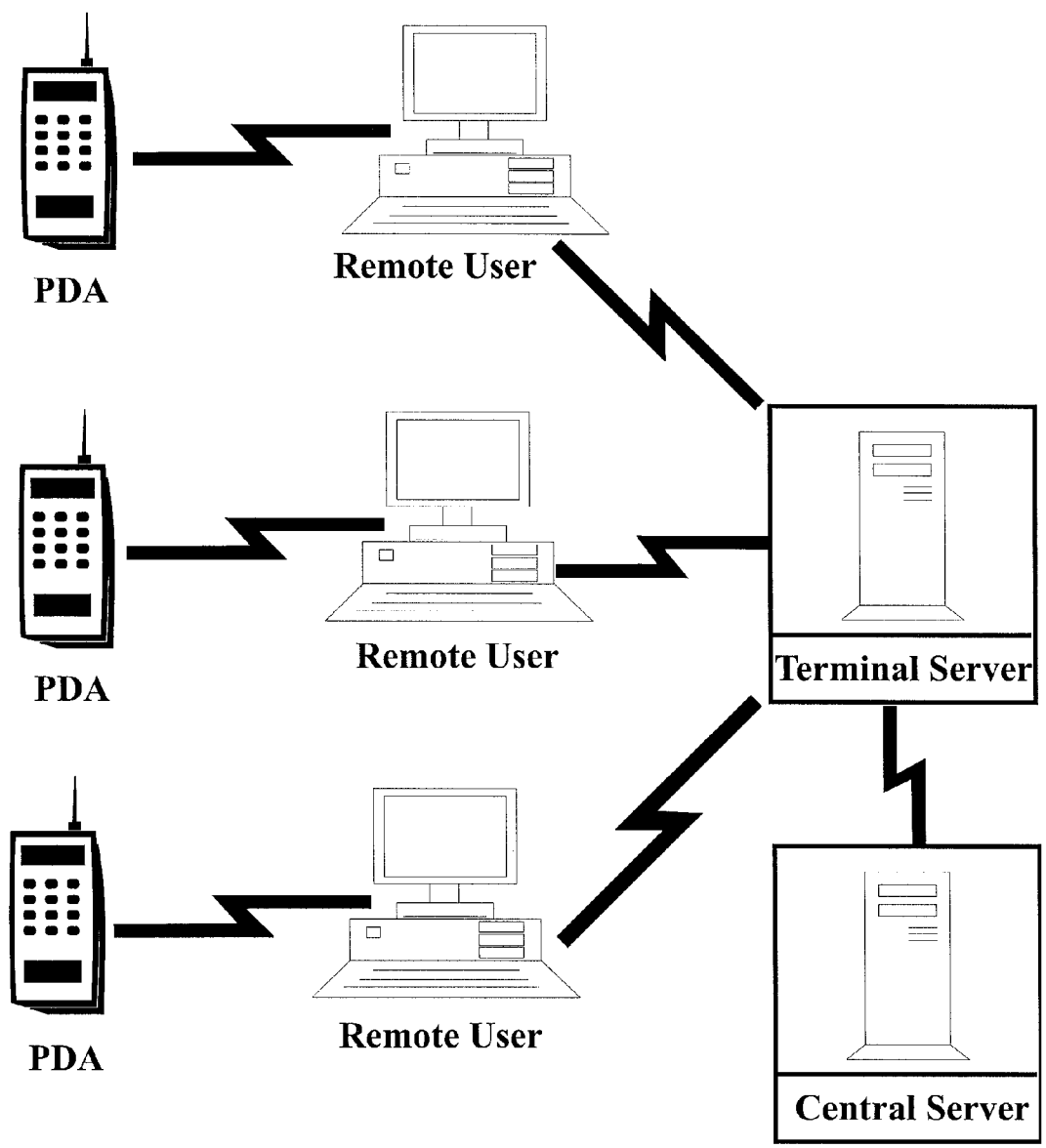
FIG. 1 is a schematic view of the secure virtual private network that may be used to implement the first preferred embodiment of the invention.

The secure virtual private network ("VPN") that may be used to implement the first preferred embodiment of the invention is shown schematically in FIG. 1. Doctors, nurses and hospital staff members may use hand held devices such as personal digital assistants ("PDAs") to link to remote user personal computers, which are linked to terminal servers (which may be located in doctors' offices, hospitals or other locations), which are linked to central servers, on which are maintained the data bases used in the invention.

Figure 2:
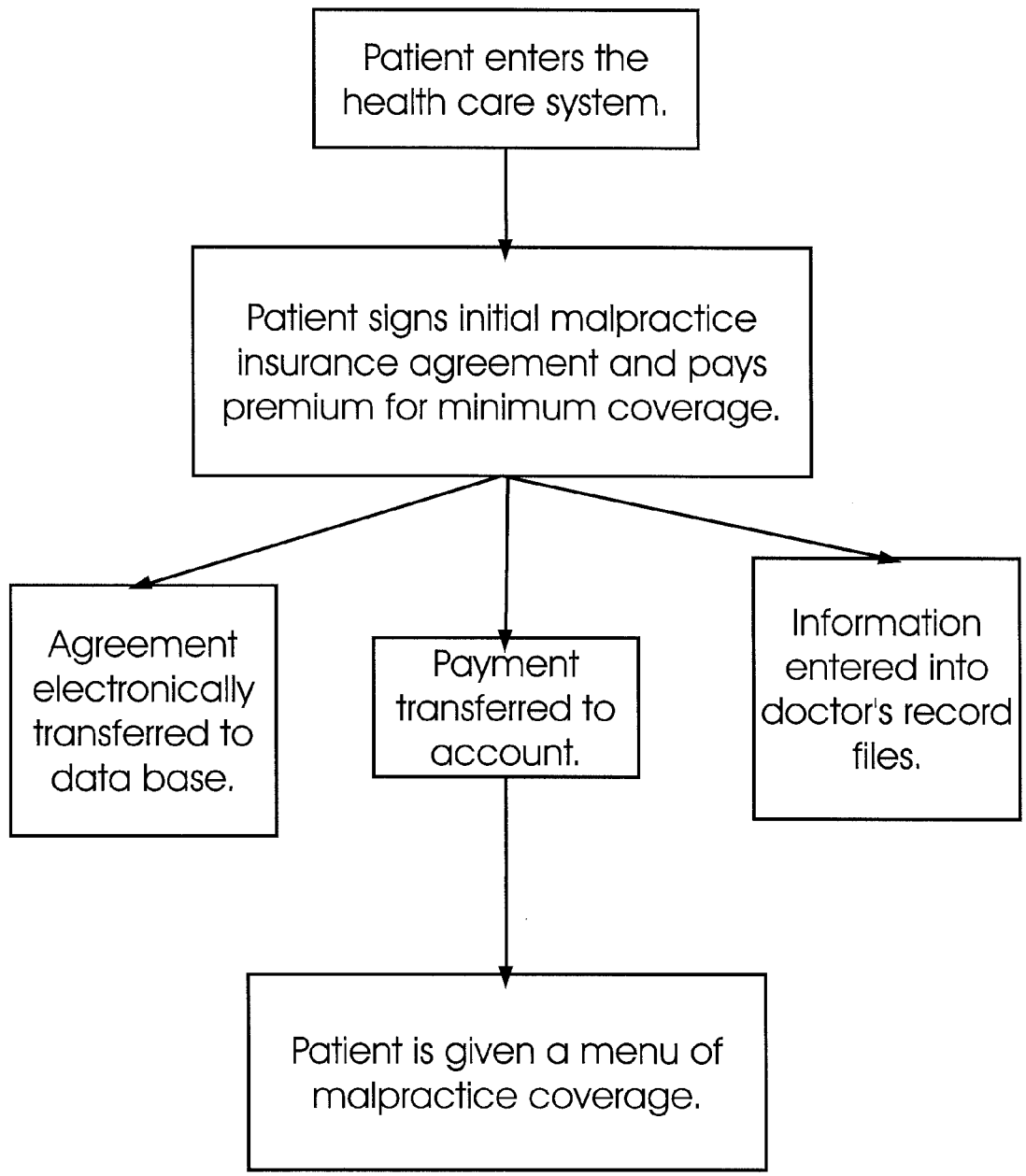
FIG. 2 is a flowchart of the initial steps in the first preferred embodiment of the invention.

The initial steps in the first preferred embodiment are summarized in the flowchart in FIG. 2. A patient (or client or other consumer) first enters the health care (or legal or other) system seeking care (or other services). (Hereinafter, only the medical application will always be discussed, but the invention may be adapted for other professions with a few obvious changes.) The consumer signs an agreement and pays a fee as a precondition to entering the system. (In the case of a minor, the consumer or patient's parent(s) or guardian(s) may sign on his or her behalf, and make the choices explained below for the minor.) The agreement guarantees compensation for malpractice up to a set maximum amount, called the "policy limit". The amount of the premium the consumer is willing to pay determines the maximum amount of the coverage. However, the patient is initially provided coverage only for a minimum policy limit, for a nominal fee (e.g., ten dollars) which may be considered as a processing charge. The doctor may even deduct the nominal fee from the doctor's fee for the initial office visit, so that it is a "free leader" for which no extra charge is imposed on the patient.

The agreement is electronically transferred to a data base. The consumer's payment is transferred to an account. Information is also entered into the professional's record files.

The consumer now has malpractice insurance coverage, up to the initial policy limit, before any services have been provided by the professional. The policy limit is disclosed to the consumer and agreed to by the consumer in the agreement signed by the consumer.

Figure 3:
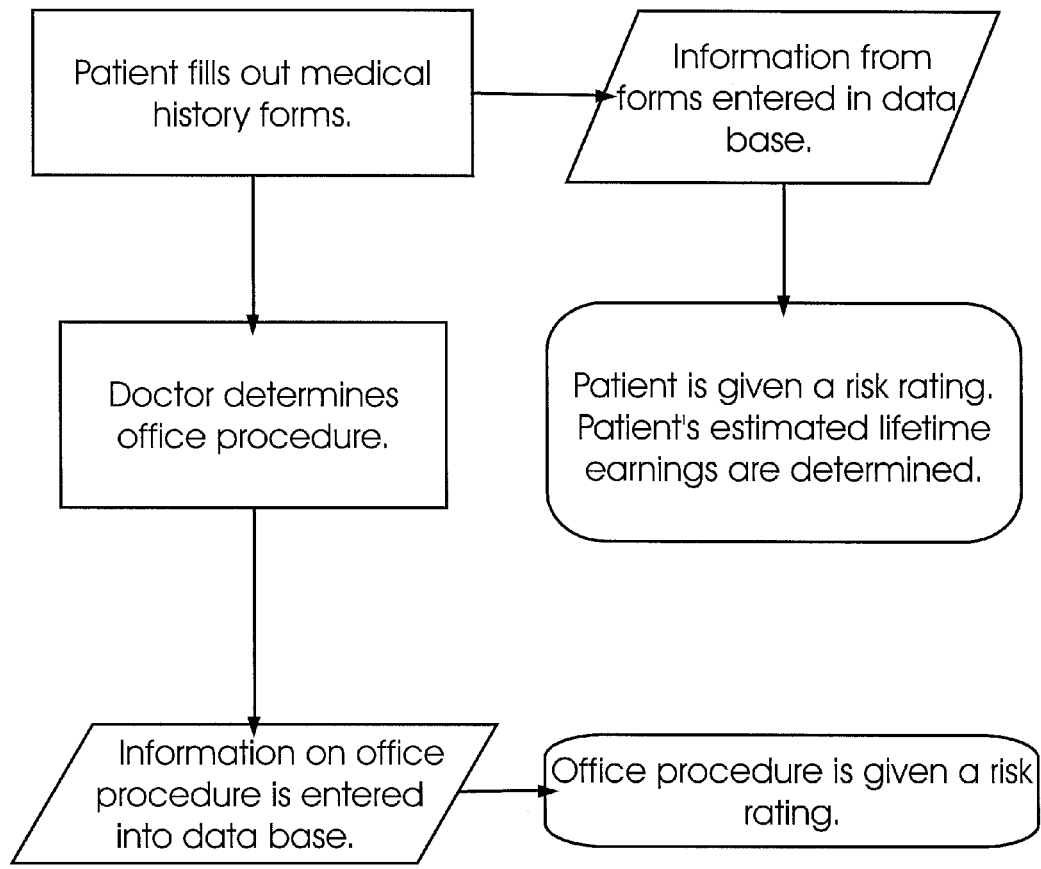
FIG. 3 is a flowchart of intermediate steps in the first preferred embodiment of the invention.

The following steps are summarized in the flowchart in FIG. 3. The patient then fills out a medical history form designed by the insurance company, as well as the doctor's medical hospital form. The forms may warn the patient that if the information provided is not true and complete, the patient will forfeit any right to compensation for malpractice. The information provided includes the patient's age, health and medical history, family history, occupation, life style, habits, work, play, and/or other objective or subjective criteria. (Other information relevant to consumer risk factors could be provided for other professions.) This information is then electronically transferred to a data base. The patient is then given a risk rating based on the information, with a certain number of points given for each negative factor (or combinations of negative factors). The patient's estimated lifetime earnings are also calculated. The doctor then determines office procedure, and that is also transferred to the data base.

The office procedure is given a risk rating. Codes for medical procedures may be taken from the American Medical Association's Current Procedural Terminology ("C.P.T." charts). Codes for diseases may be taken from the World Health Organization's International Classification of Diseases ("ICD-9" or "ICD-10" charts). A table may be developed, such as the Diagnosis Related Groups ("D.R.G."—developed by the insurance industry), with codes for medical procedures on one axis, and codes for diseases on the other axis. Each cell in the table would represent the combination of one disease with one procedure, and would be assigned a number of points based on the riskiness of the combination, with more points assigned to riskier combinations. Alternatively, procedures could be given ratings based on other objective and/or subjective criteria. (Risk ratings for services provided by other professions could be developed for those other professions.)

Figure 4:
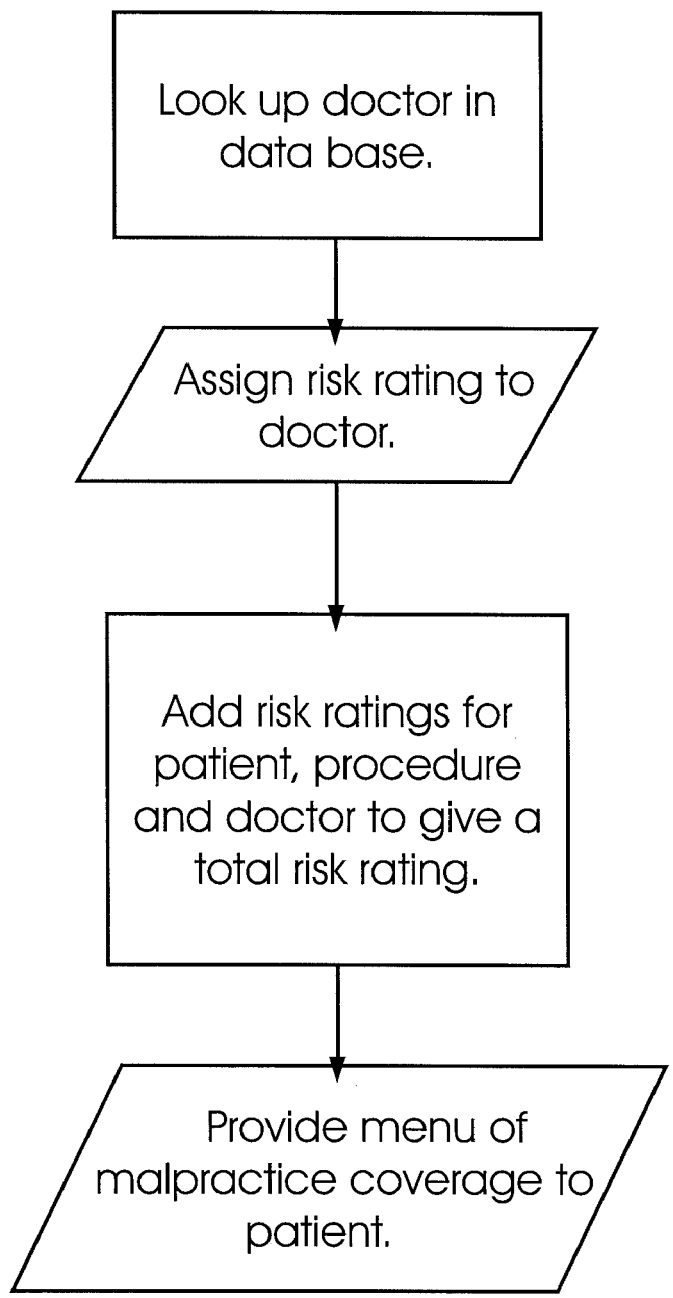
FIG. 4 is a flowchart of the final steps in the first preferred embodiment of the invention.

The following steps are summarized in the flow chart in FIG. 4. A national data base containing information on doctors is checked and the doctor is given a risk rating. The data base includes information on each doctor's field of expertise, malpractice or other complaints made against the doctor, any physical or mental disabilities that the doctor is known to have, and/or other objective or subjective criteria. The doctor will be given a certain number of points for each negative factor (or combination of negative factors). (National data bases for other professions could also be developed for those professions.)

The risk rating for the patient, the doctor, and the procedure are then added to give a total risk rating. (Alternatively, they may be combined mathematically in other ways than simple addition.) The higher the total risk rating, the more costly the patient's malpractice insurance coverage will be. The patients can choose the coverage they want, ranging from basic coverage to extreme coverage. The patient is provided with a menu of malpractice coverage. They choose the coverage amount and pay the corresponding premium. For example, for illustration only:

| Policy Limit | Premium |
|---|---|
| $ 100,000.00 | $ 10.00 |
| $ 200,000.00 | $ 20.00 |
| $ 300,000.00 | $ 30.00 |
| $10,000,000.00 | $1,000.00 |

A menu of insurance for lost earnings over the patient's future lifetime could be offered separately, based on the patient's estimated lifetime earnings.

Figure 5:
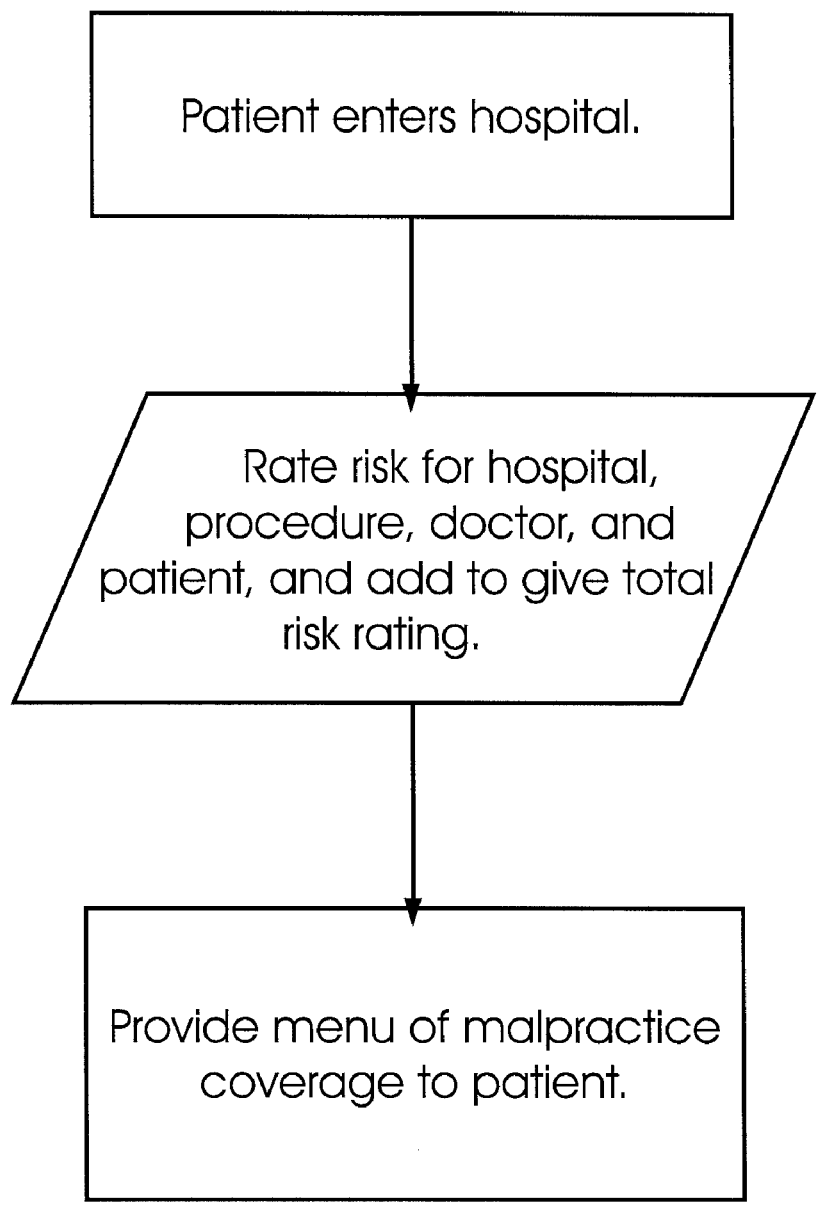
FIG. 5 is a flowchart summarizing the steps taken in the first preferred embodiment when a patient is admitted to a hospital.

The procedure followed when a patient enters a hospital (or other health care institution) is summarized in FIG. 5. If the patient enters a hospital, then the following steps are performed:

(a) The hospital's risk is rated. Factors used in determining the hospital's risk may include its size, location, the history of complaints against the hospital or against doctors at the hospital for malpractice, the ratio of nurses to beds, the ratio of specialists to beds, and/or other objective or subjective criteria. Points are given for each negative factor (or combination of factors).

(b) The risk of the procedure to be performed in the hospital is rated.

(c) The risk for each doctor or other individual health care provider involved in the procedure is rated.

(d) The patient's risk is rated.

The ratings in (a) through (d) are added together to give a total risk rating. As above, the patient is then provided with menu of malpractice coverage, with premiums determined by the total risk rating and the policy limits chosen by the patient.

Computers will be used to calculate the risk ratings and premiums. The data bases will be maintained on computers.

Figure 6:
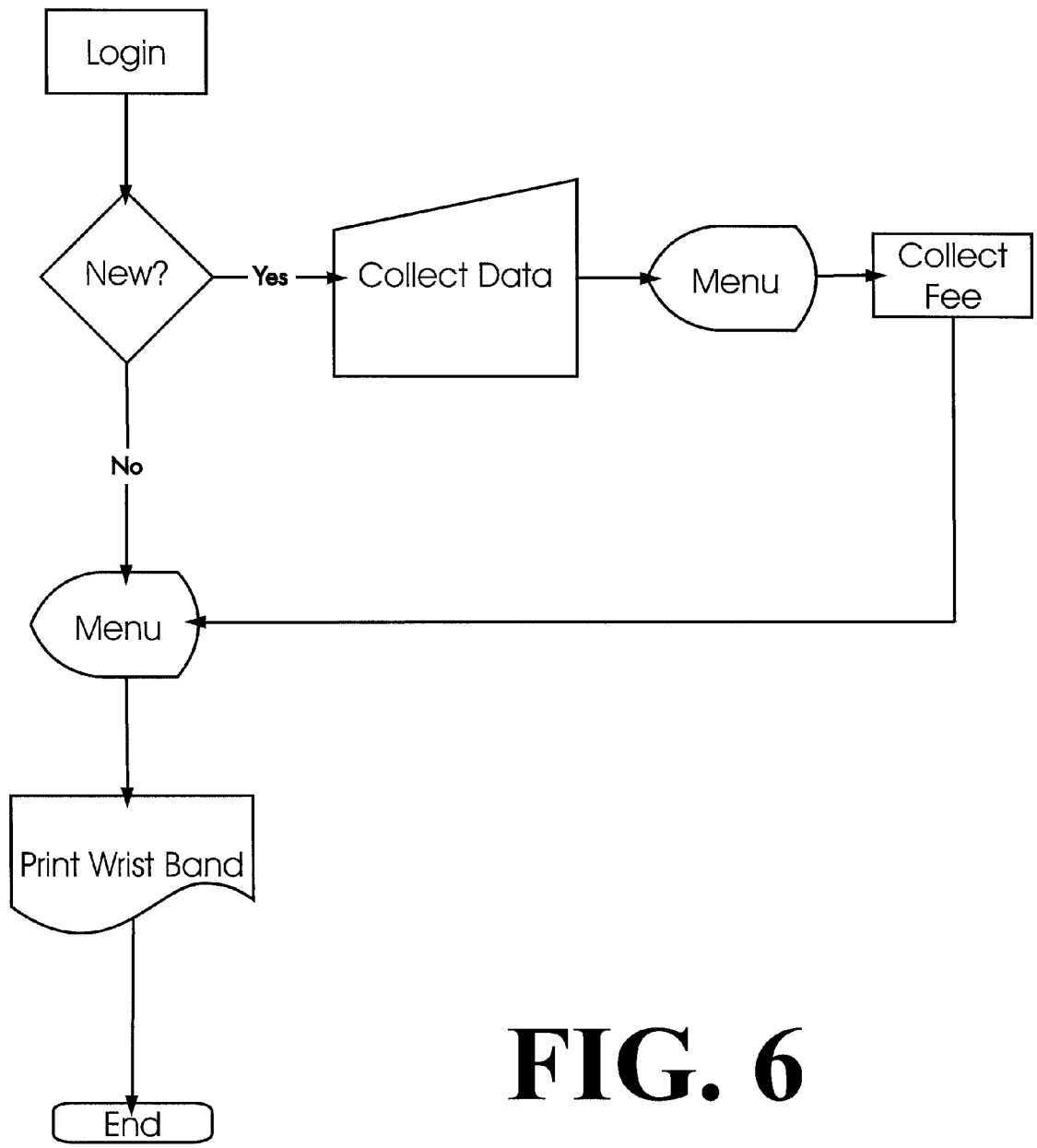
FIG. 6 is a flowchart summarizing the steps taken in patient interaction with the system of the first preferred embodiment of the invention.

The steps taken in patient interaction with the system are summarized in FIG. 6. The patient (or a staff member acting for the patient) logs into the system. If the patient is a new patient, background information and data about, current medical problems of the patient are collected. The patient is then presented with a menu of malpractice coverage. A fee is collected, and the patient is presented with a second menu. If the patient is not a new patient, then the second menu is presented as soon as it is determined that the patient is not a new patient. Data are then encoded in a "smart" electronic wristband worn by the patient.

Figure 7:
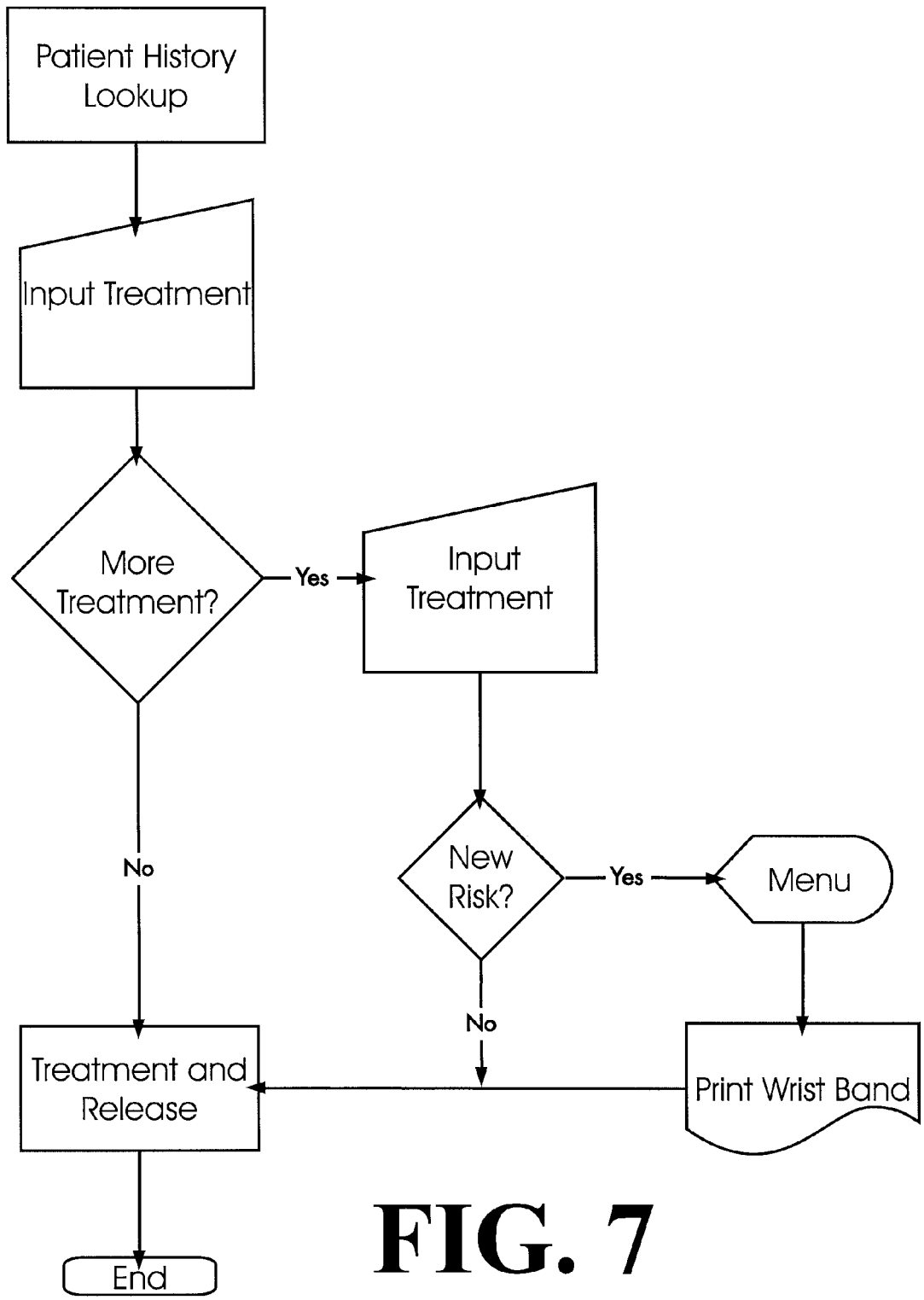
FIG. 7 is a flowchart summarizing the steps taken in doctor-patient interaction in the first preferred embodiment of the invention.

Doctor-patient interaction is summarized in FIG. 7. The doctor (or a staff member) looks up the patient's history on the computer system. The doctor inputs the treatment that has been given to the patient. If more treatments are to be given, then the doctor inputs the new treatments to be provided. If the new treatments will create new risk, the patient is then provided with a menu of malpractice coverage, data are encoded on the patient's wristband, the new treatments are then provided, and the patient is released. If the new treatments will not involve any additional risk, then the new treatments are provided without further ado, and the patient is released. If no new treatments are to be provided, then the old treatments are again given, and the patient is released.

Figure 8:
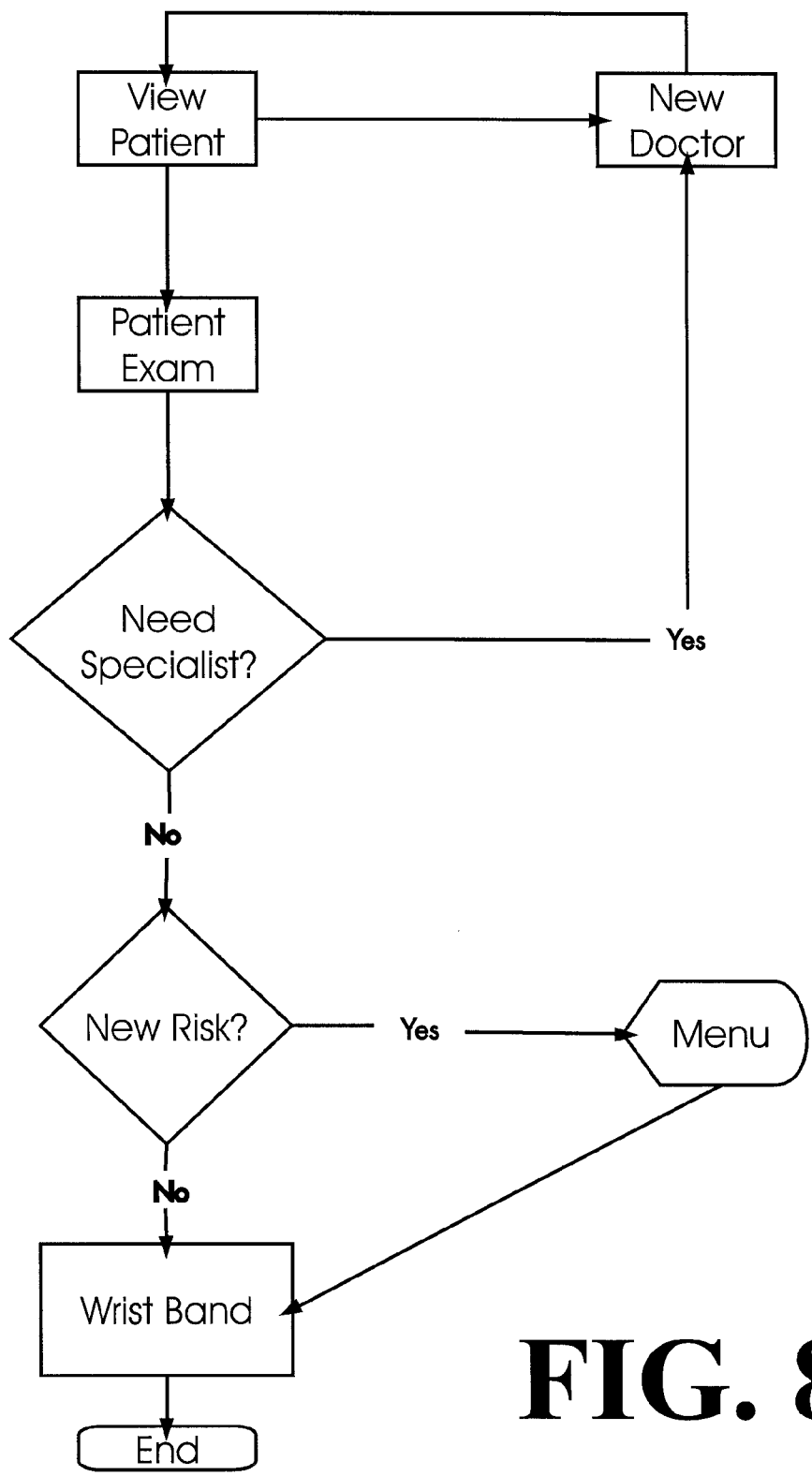
FIG. 8 is a flowchart summarizing the steps relating to a wrist band when a patient is admitted to a hospital in the first preferred embodiment of the invention.

The risk ratings may be encoded on a wrist band worn by a patient. FIG. 8 summarizes the procedure when a patient is admitted to a hospital. When a doctor first views the patient, he or she may decide to refer the patient to a new doctor right away (who will then return to the first step of viewing the patient). Otherwise, the doctor examines the patient. After the examination, the doctor may decide to refer the patient to a specialist (who will return to the first step of viewing the patient); otherwise, the doctor will determine if a new risk evaluation of the patient is necessary. After a new risk evaluation, the patient will be given a malpractice menu, as discussed above. Whether or not there is a new risk evaluation, the final step is to encode the risk factors onto a wrist band to be worn by the patient. The encoding may utilize a smart chip embedded in the wrist band, or color coding or a bar code on the wrist band.

Figure 9:
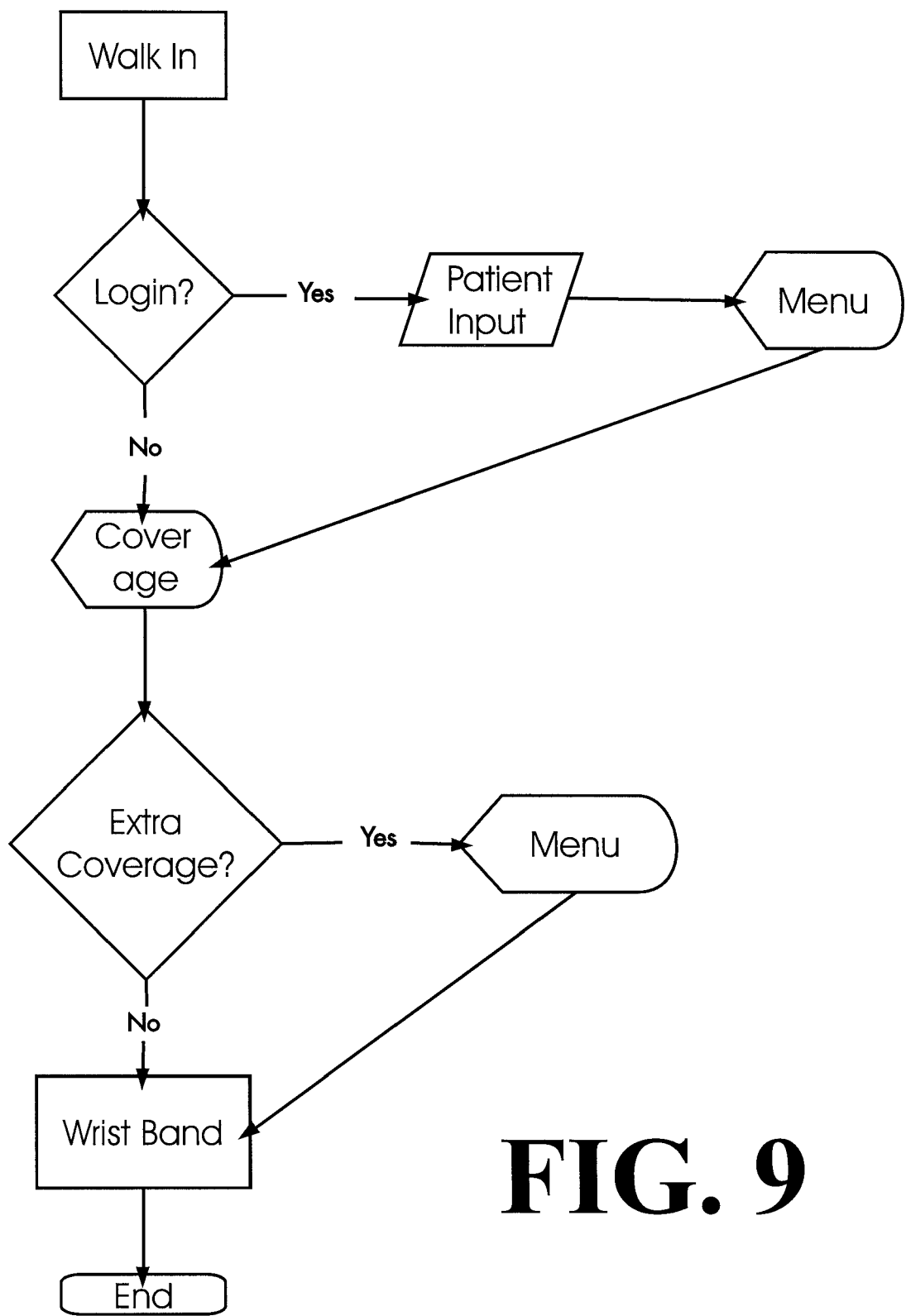
FIG. 9 is a flowchart summarizing the steps relating to a wrist band for a walk-in patient at a hospital in the first preferred embodiment of the invention.

FIG. 9 summarizes the procedure when a patient who has already been examined is admitted to the hospital on a "walk in" basis. If the patient has not already provided the necessary information, the system is logged into, information from the patient is inputted, and the patient is given a menu. The patient then selects a level of coverage. If the patient desires extra coverage, another menu is presented. Finally, the risk factors are encoded onto a wrist band.

The second preferred embodiment is the same as the first preferred embodiment, except that what is insured against is not only malpractice, but compensation is provided to the consumer for any unfavorable outcome of the services. The following are two possible examples of unfavorable outcomes that are not malpractice, for illustration only:

1. An orthopedic surgeon reconstructs a limb damaged in an automobile or industrial accident, but one of the patient's arms or legs is shorter than the other, or there is permanent scarring or other disfiguration, through no fault of the surgeon.

2. Plastic surgery makes the appearance of a patient worse, rather than better, through no fault of the plastic surgeon.

Figure 10:
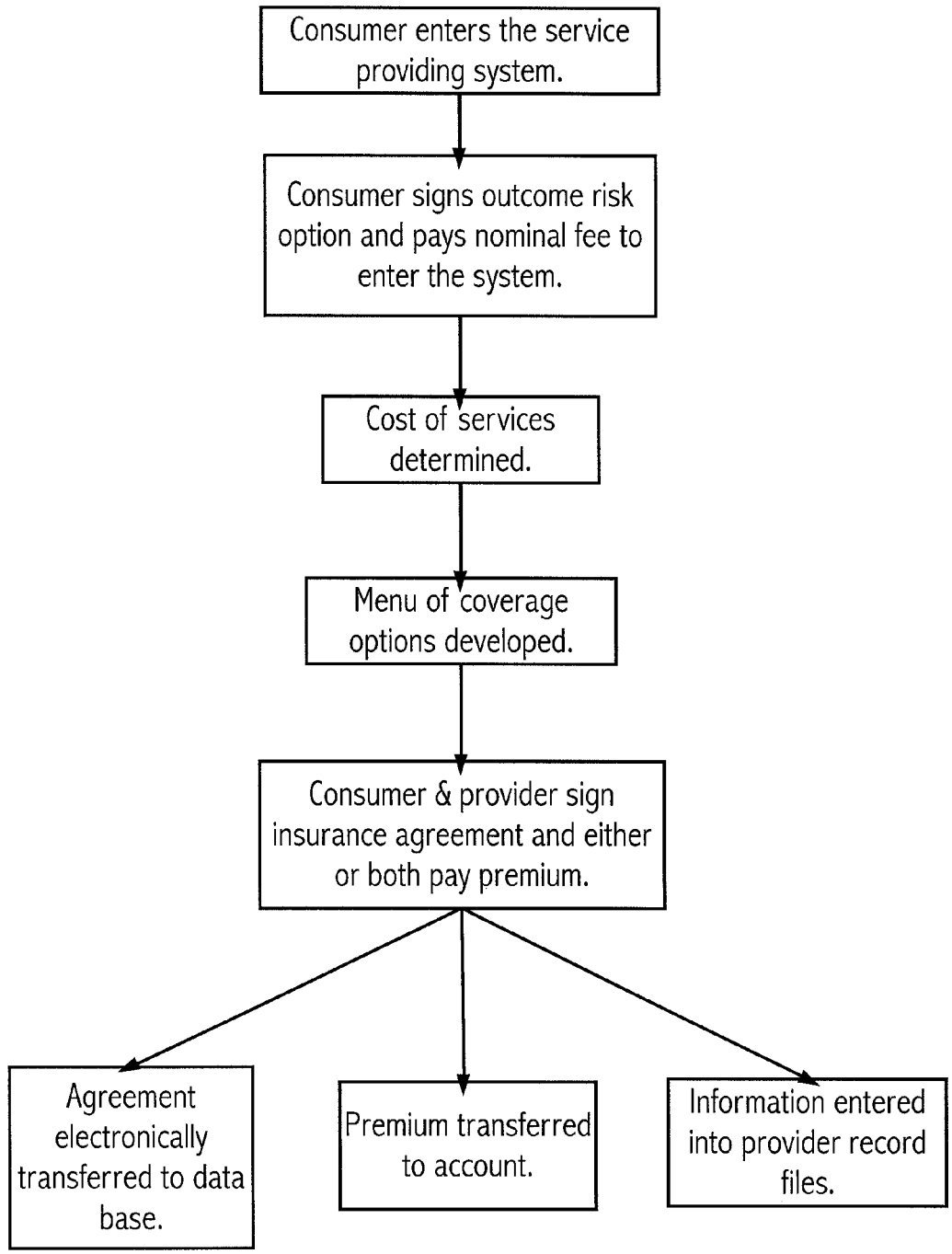
FIG. 10 is a flowchart summarizing the steps taken in the second preferred embodiment of the invention.

In such cases, the consumer would be compensated for the unfavorable outcome, even though there was no malpractice. FIG. 10 summarizes the steps taken in the second preferred embodiment of the invention. The consumer enters the (medical or other) service providing system. The consumers signs an initial agreement opting for insurance against any unfavorable outcome (which could be presented as an alternative and/or in addition to the malpractice insurance described above) and pays a nominal fee to enter the system. The cost of the services to be provided is determined. A menu of coverage options is developed. The consumer and the service provider then sign an agreement providing for unfavorable outcome insurance, and the consumer pays the premium. (Alternatively, the premium may be paid by the service provider or by both the consumer and the service provider.) The agreement is then electronically recorded and the record is transferred to a data base. The premium paid is transferred to an account. Relevant information is entered into the service provider's record files.

The third preferred embodiment is the same as the first preferred embodiment, except that the premium is paid by the doctor or other service provider.

The fourth preferred embodiment is the same as the second preferred embodiment, except that the premium is paid by the service provider.

The fifth preferred embodiment is the system of rating risks by itself, and the data bases that are created and maintained in the system, as described above, used independently of the insurance system.

Figure 11:
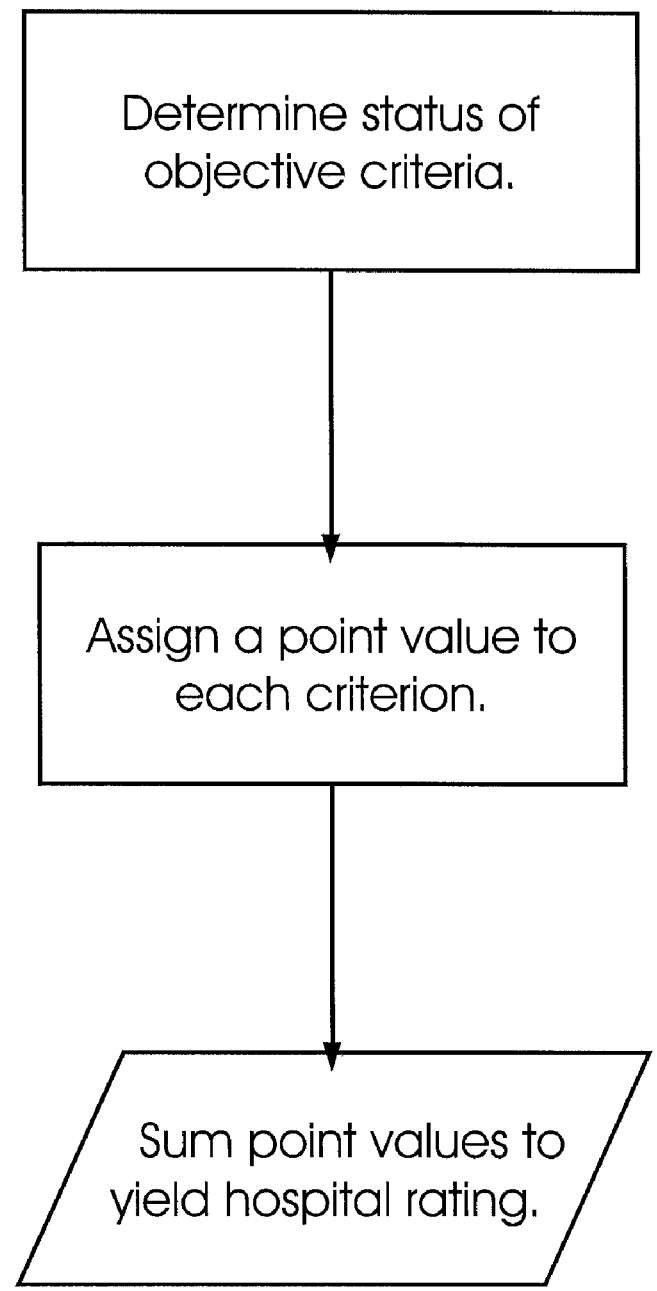
FIG. 11 is a flowchart summarizing the steps taken in the sixth preferred embodiment of the invention.

The sixth preferred embodiment is a method of rating hospitals for their risk of medical malpractice liability. The steps in the method are summarized in FIG. 11. First, the status of various objective criteria related to the hospital's risk is determined. The criteria can include, but are not limited to, the following: the number of registered nurses per bed, the number of licensed practical nurses per bed, the number of medical specialists per bed, the number of medical subspecialists per bed, whether or not the hospital is a teaching hospital, the number of hours worked per week by medical residents, the number of hours worked per day by staff persons, the number of pharmacists per bed, whether or not drug dispensing is automated, the financial status of the hospital, the income-generating ability of the hospital, the credit rating of the hospital, whether or not nuclear medicine is practiced at the hospital, the socioeconomic status of the area in which the hospital is located, how easy it is for the public to get to the hospital (e.g., proximity to major highways or public transit), the types of insurance coverage that the hospital has, and the policy limits of each type, the occupational, educational and/or social backgrounds of the members of the hospital's governing board, the number of physicians, interns, residents, nurses and other staff in the hospital's emergency room, the types of infectious diseases treated at the hospital, and the number of patients having each type, the number of cardiology procedures done each year, and the types of other medical procedures performed at the hospital, and the number of each type performed in a given time period. A point value is then assigned to each criterion. A variety of possible methods may be used to assign point value. Where there is a simple "yes" or "no" answer to whether or not a criterion is present (i.e., whether or not the hospital is a teaching hospital) a "yes" answer could be assigned a value of 1, and a "no" answer a value of 0, multiplied by a fixed number of points. Where the criterion has a range of possible numerical values, the range can be divided into several intervals, with the numerical values within each interval being given a certain fixed number of points. Alternatively, the numerical value can be multiplied by a constant, or other mathematical operations can be performed to yield the point value for the criterion. An overall rating for the hospital is then determined from the point values for the criteria. The rating may be determined by simply adding the point values. Alternatively, other mathematical operations may be performed on the point values for the criteria to yield the rating. The rating may be used by insurance companies, or by the hospital for self-evaluation.

In the sixth preferred embodiment, the objective criteria are five or more criteria selected from the group comprising (where the letters may represent any constant):

the number of registered nurses per bed times A;

the number of licensed practical nurses per bed times B;

the number of medical specialists per bed times C;

the number of medical subspecialists per bed times D;

whether or not the hospital is a teaching hospital, with E points awarded if it is;

the mean number of hours worked per week by medical residents, times F;

the mean number of hours worked per day by staff persons, times G;

the number of pharmacists per bed times H;

whether or not drug dispensing is automated, with I points awarded if it is;

the financial status of the hospital, with negative J points for each thousand dollars it is in debt;

the income-generating ability of the hospital, with positive K points for each thousand dollars of annual profits, and negative K points for each thousand dollars of annual losses;

whether or not nuclear medicine is practiced at the hospital, with L points awarded if it is;

the socioeconomic status of the area in which the hospital is located, determined by the difference between the mean income of the population residing within a radius of M miles from the hospital and the national mean income, times N per thousand dollars of annual income;

how easy it is for the public to get to the hospital, determined by mean number of minutes that it takes emergency vehicles to arrive at the hospital from within a given radius, after a patient has entered the vehicle and it has been cleared to proceed to the hospital, divided by the distance in miles from the hospital, times P;

the types of insurance coverage that the hospital has, and the policy limits of each type, determined by the difference between the insurance premiums paid by the hospital and the national mean insurance premiums paid by hospitals with the same numbers of beds, times Q;

the occupational, educational and/or social backgrounds of the members of the hospital's governing board, determined by the mean number of years of college completed times R, and by the percentage who are United States citizens times S;

the number of physicians, interns, residents, nurses and other staff in the hospital's emergency room times T;

the number of types of infectious diseases treated at the hospital, times the number of patients having each type, times U;

the number of cardiology procedures done each year times V; and the number of other types of other medical procedures performed at the hospital, and the number of each type performed annually, times W.

Alternatively, ten or more, fifteen or more, or all of the criteria given above may be selected.

Figure 12:
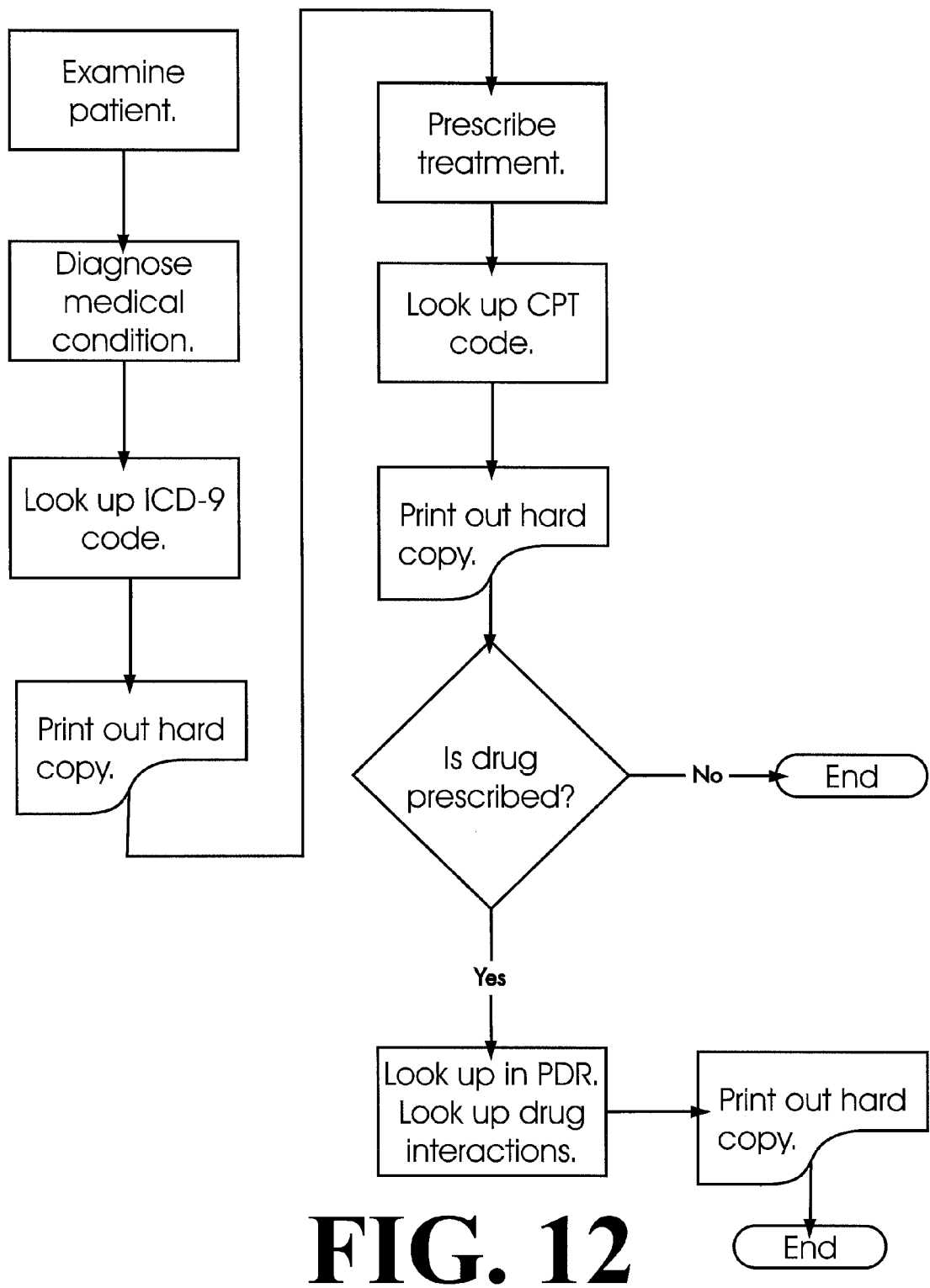
FIG. 12 is a flowchart summarizing the steps taken in the seventh preferred embodiment of the invention.

The seventh preferred embodiment is a method of reducing the risks of malpractice or other unfavorable outcomes. The steps in the method are summarized in FIG. 12. A patient is first examined by a doctor or other health care provider. (For the sake of simplicity, all health care providers will hereinafter be referred to as "the doctor".) The doctor then diagnoses any medical condition that the patient has, and assigns a predetermined code to the medical condition. The doctor may look up the code in a manual such as ICD-9 or ICD-10 (referred to above). The manual may be in paper form ("hard copy") or online, and may also assist in diagnosis. The code is then entered into an automated system, and stored information about the medical condition that the code represents is displayed on a computer monitor and/or printed out.

The doctor may then prescribe one or more treatments for each diagnosed medical condition of the patient, and assign a predetermined code to any treatment. The doctor may look up the code in a reference such as the C.P.T. charts (referred to above). The reference may be in paper form or online, and may also assist the doctor in determining which treatment to prescribe. Again, the code is entered into the automated system, and stored information about the treatment that the code represents is displayed on a computer monitor and/or printed out. If the treatment prescribed is a drug, the doctor may then look up the drug in a manual such as the Physicians' Desk Reference ("PDR"), which again may be in paper form or online, and may assist the doctor in determining what drug to prescribe. The doctor may also look up interactions between drugs in a separate data base. Once again, the code is entered into the automated system, and stored information about the drug that the code represents is displayed on a computer monitor and/or printed out.

If the information regarding medical conditions, treatments and drugs is displayed on monitors, both the doctor and the patient should be able to view a monitor. If it is printed out, both the doctor and the patient should have a hard copy. After reviewing the information, the patient may be able to assist the doctor in reducing the risk of an unfavorable outcome, by bringing facts previously known to the patient to the doctor's attention, that the doctor may not have inquired about, and that the patient may not have recognized as being relevant. It will also help insure that the consent of the patient to any treatment is fully informed.

Figure 13:
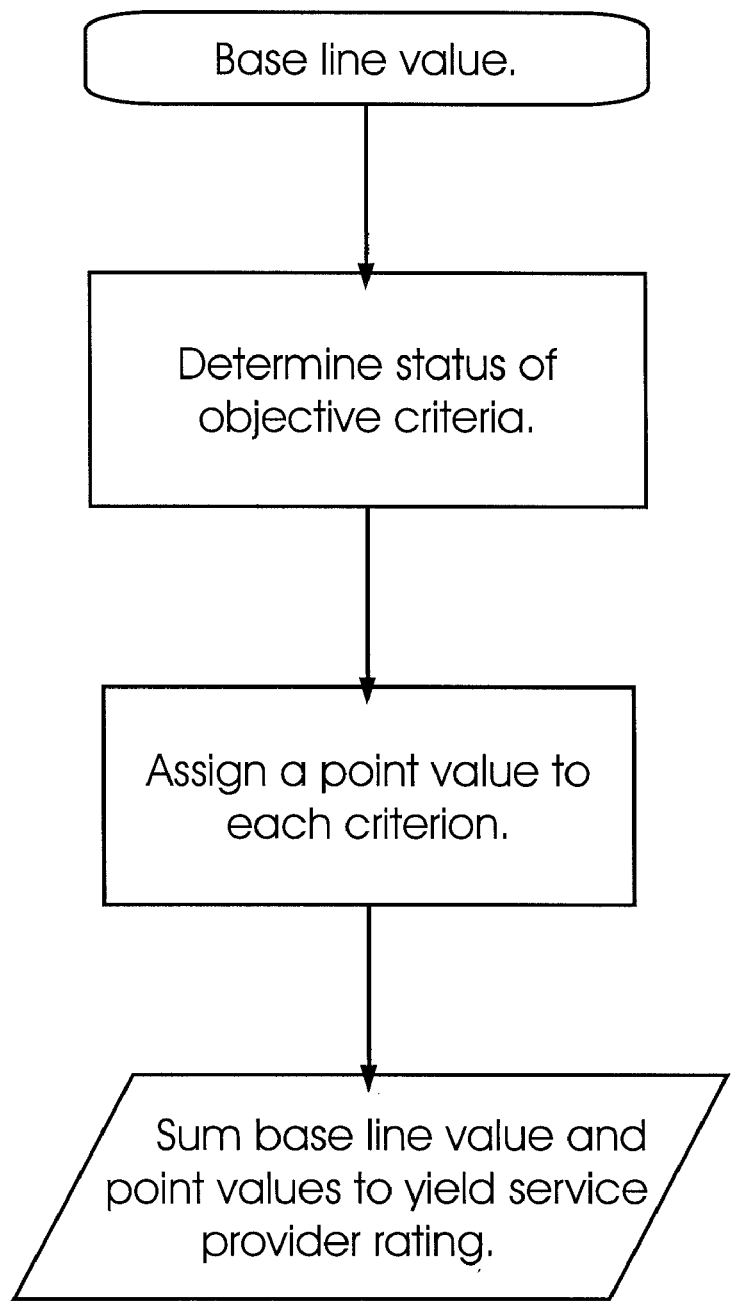
FIG. 13 is a flowchart summarizing the steps taken in the eighth preferred embodiment of the invention.

The eighth preferred embodiment is a method of rating a service provider for risk of malpractice (or other unfavorable outcomes). The service provider (hereinafter referred to as "the provider") may be a health care service provider, such as a physician, dentist or veterinarian, or another professional, such as a lawyer. The steps in the method are summarized in FIG. 13. The provider is initially given a base line value of X points (where X may be any constant). The status of various objective criteria is then determined. Point values are assigned to each criterion based on its status. The base line value and the point values are then summed to yield an overall rating for the provider. (Alternatively, other mathematical operations may be performed on the point values to yield the overall rating.) Negative point values are assigned to criteria having a beneficial status, and positive point values are assigned to criteria having a detrimental status. (Alternatively, positive point values may be assigned to criteria having a beneficial status, and negative point values may be assigned to criteria having a detrimental status.) The provider may be awarded a set number of negative (or positive) points at the ends of specified periods if the service provider has had no unfavorable outcomes during each period.

Positive (or negative) point values may be given to criteria that include, but are not limited to, the following (where the letters may represent any constant): excessive consumer complaints about a service provider (with a number of complaints exceeding Y being given Z points), excessive entries in a data base of detrimental information, such as the national data base referred to above (with a service provider having more than AA entries being given BB points), actions taken against the provider by a governing body, such as a licensing board (with CC points for each such action), censorship of the service provider by the governing body (with DD points each time the service provider is so censored), malpractice judgments against the service provider (with EE points for each time the service provider is found liable for malpractice by a court), and settlements of malpractice claims in which the service provider paid damages (with KK points for each time the service provider agreed to a settlement with damages). For the last two criteria, positive (or negative) point values may be given in proportion to the amount of any damages awarded (in a judgment or settlement) against the provider for malpractice. Negative (or positive) point values may be given to criteria that include, but are not limited to, the following: work by a specialist within his or her specialty (the percentage of time that a specialist works within his or her specialty time FF), work by a subspecialist within his or her subspecialty (the percentage of time that a subspecialist works with his or her subspecialty time GG), participation by the provider in continuing professional education related to his or her work (to be awarded HH points), commendation of the provider by a governing body (to be awarded II points), and the number of unfavorable outcomes, with the service provider is awarded JJ points at the end of a year if the service provider has had no unfavorable outcomes during the year.

The rating may be used by insurance companies, or by the provider for self-evaluation. If negative point values are assigned to criteria having a beneficial status, and positive point values are assigned to criteria having a detrimental status, then a standard premium could be multiplied by the rating to give the premium that the provider would be charged. If positive point values are assigned to criteria having a beneficial status, and negative point values are assigned to criteria having a detrimental status, then a standard premium could be divided by the rating to give the premium that the provider would be charged.

Figure 14:
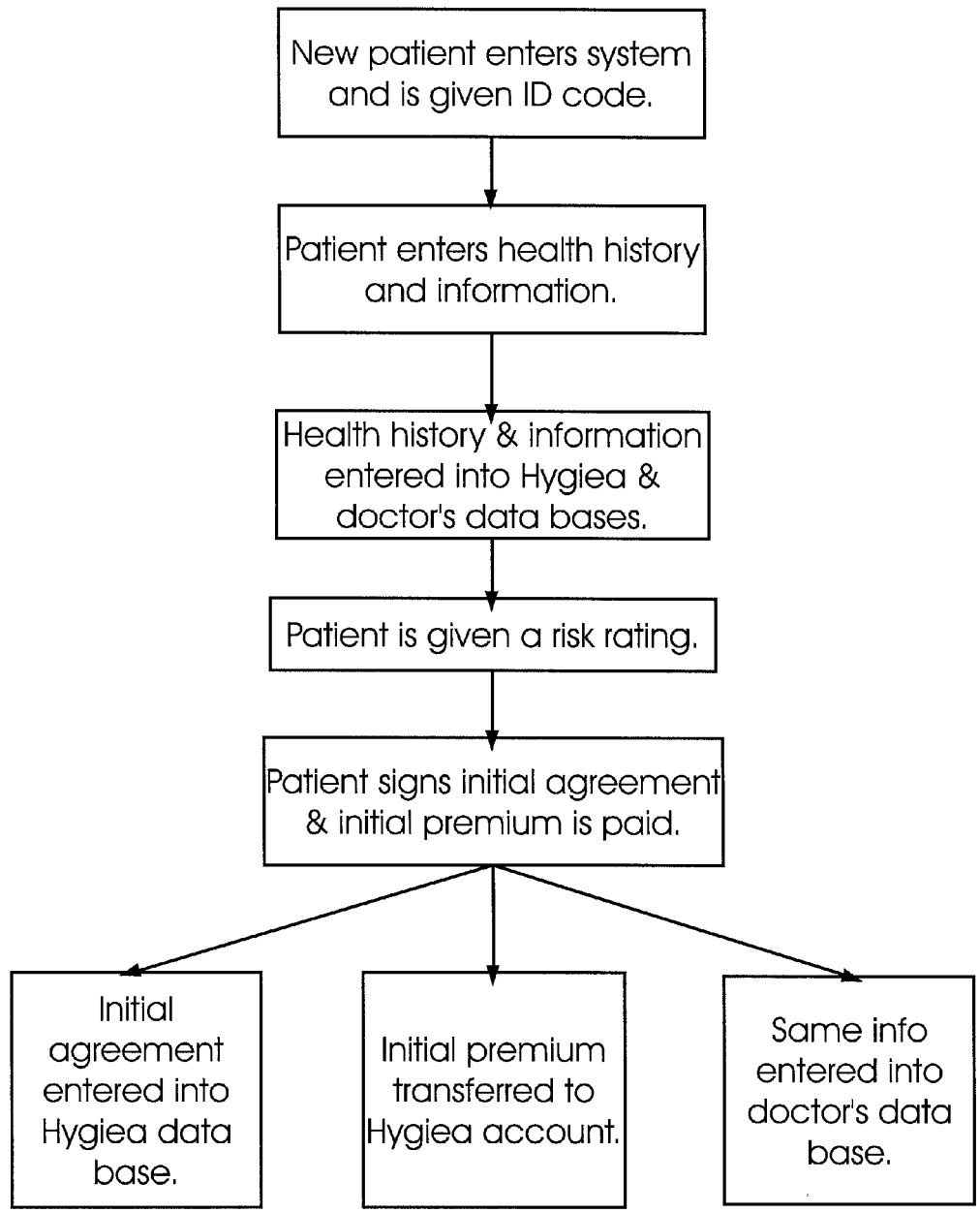
FIG. 14 is a flowchart summarizing a first series of steps taken in the ninth preferred embodiment of the invention when a new patient enters the system.

The ninth preferred embodiment is an alternative method of providing medical malpractice insurance, which is an adaptation and modification of the first preferred embodiment. The first steps in the method when a new patient enters the system are illustrated in the flowchart in FIG. 14. (Hereinafter, a hypothetical company that administers the system will be referred to as "Hygiea".) A patient enters the Hygiea Health Care System and is given an identification number. The patient then fills out one or more forms (on paper or on-line) providing his (or her) health history and other information required by Hygiea. The information is then entered into Hygiea's data base and the doctor's data base. The patient is then given a risk rating. Next, the patient signs an initial malpractice insurance agreement. The patient and/or the doctor pay the initial premium for malpractice insurance coverage. (The doctor may include the premium in his (or her) billing statement, but the premium should be pre-paid at this time.) The signed agreement is then electronically transferred into Hygiea's data base. The initial premium payment is electronically transferred to Hygiea's account. And information about the agreement and the premium payment is simultaneously entered into the doctor's data base.

Figure 15:
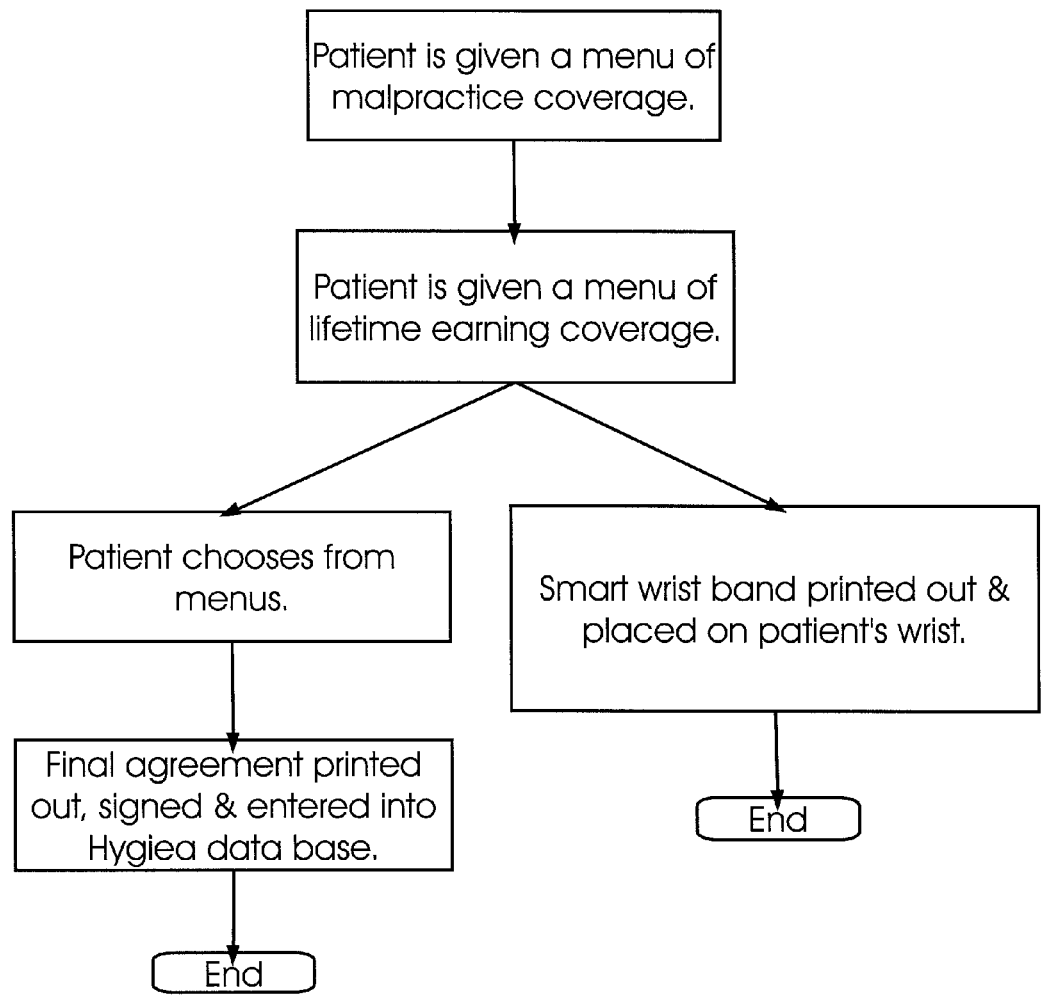
FIG. 15 is a flowchart summarizing a second series of steps taken in the ninth preferred embodiment of the invention when a new patient enters the system.

The next steps are shown in FIG. 15. The patient is given a menu of malpractice insurance coverage, ranging from a required minimum coverage at a minimum cost to maximum coverage at a maximum cost. The patient is then given a menu of optional lifetime earning coverage (that will compensate them for lost earnings due to medical malpractice or other unfavorable outcomes) with a range between zero coverage at no cost to maximum coverage at a maximum cost. The patient makes his choices from the menus, selects a payment mode, and a final agreement is printed out. When the final agreement is signed by the patient, it is entered into the Hygiea data base and payments are transferred into the Hygiea account. Simultaneously, a smart wrist band is printed out (containing the information provided earlier) and placed on the patient.

Figure 16:
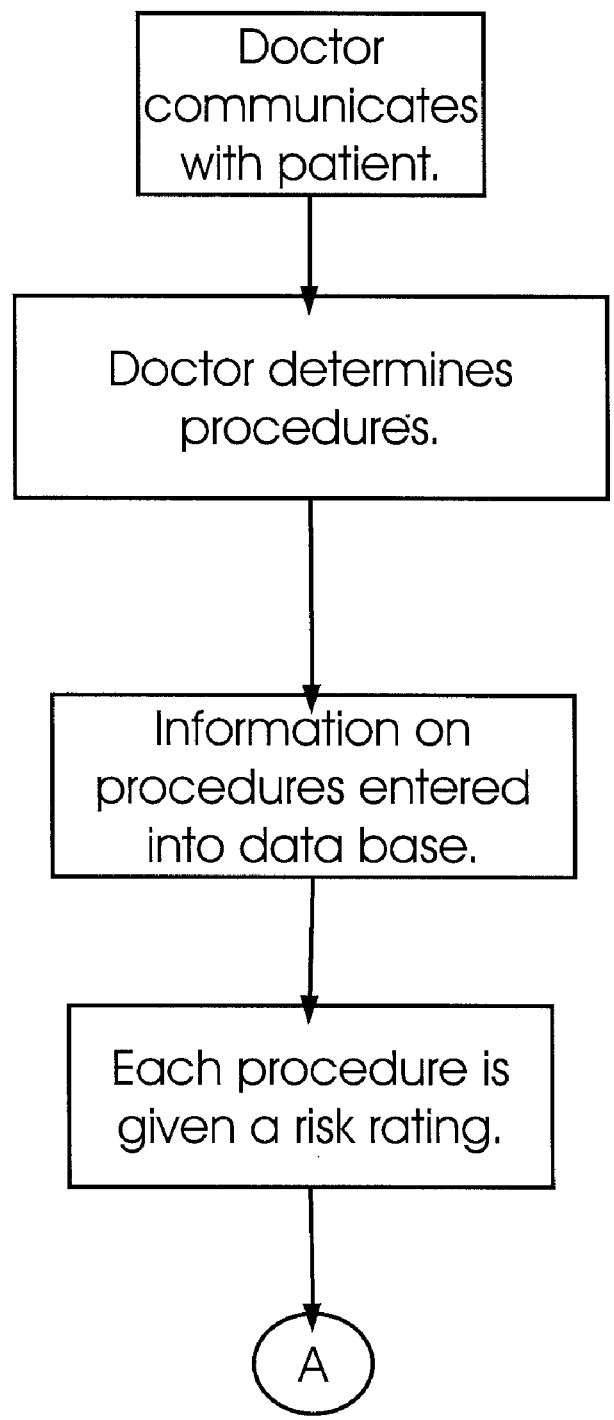
FIG. 16 is a flowchart summarizing a third series of steps taken in the ninth preferred embodiment of the invention when a new patient enters the system.

FIG. 16 shows further steps in the process. The doctor communicates with the patient, either face to face in a traditional office visit, or electronically or by other means. The doctor determines medical procedures to be performed. Information on the procedures is entered into a data base. Each procedure is given a risk rating.

Figure 17:
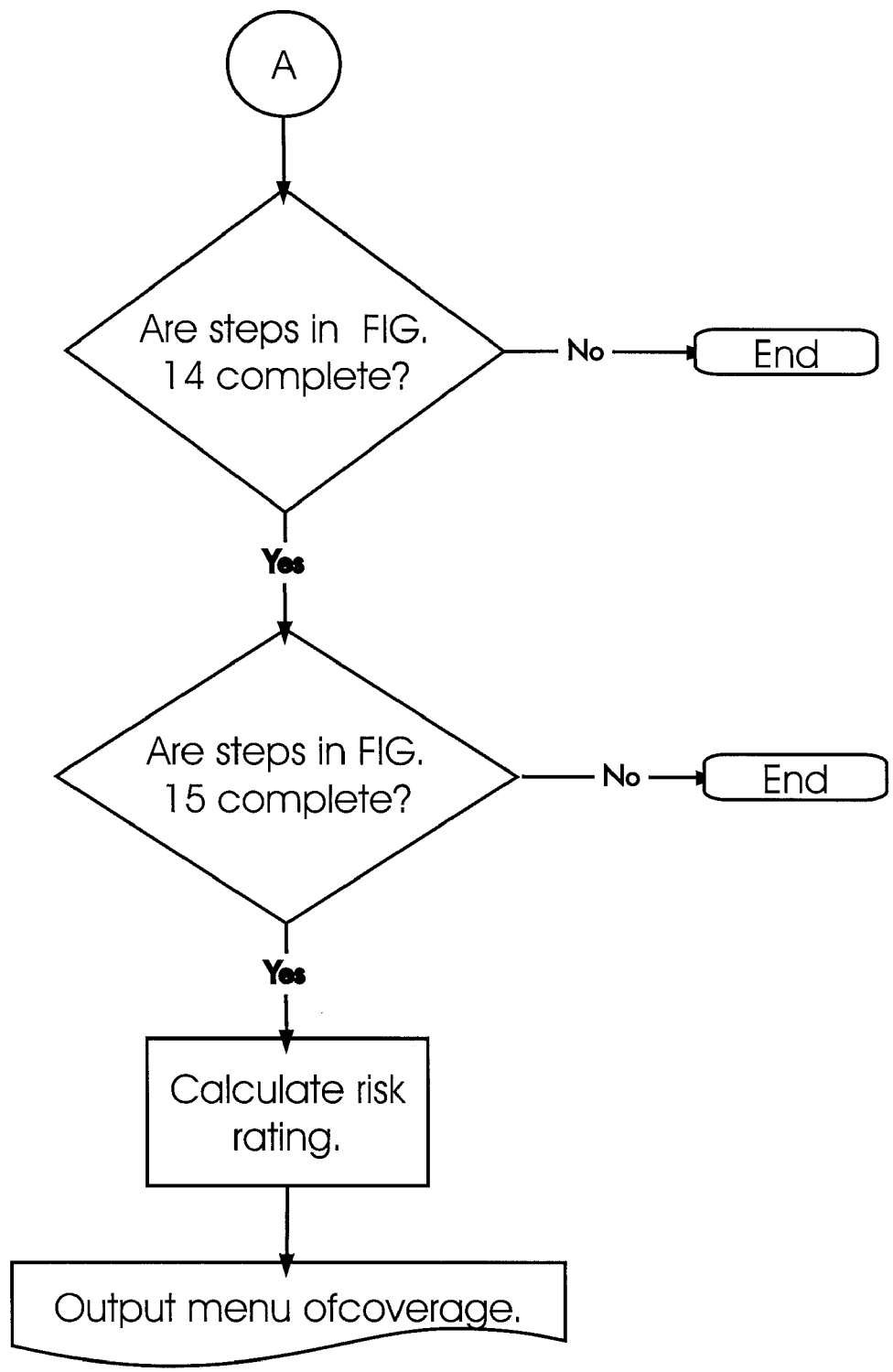
FIG. 17 is a flowchart summarizing a fourth series of steps taken in the ninth preferred embodiment of the invention when a new patient enters the system.

FIG. 17 shows the concluding steps in the process for a new patient. First, the systems checks to make sure that the steps shown in FIGS. 14 and 15 have been completed. Then a risk rating is calculated, and a menu of malpractice coverage is provided to the patient and the doctor. Note that this is additional coverage for the specific procedure, and is in addition to the coverage mentioned above.

Figure 18:
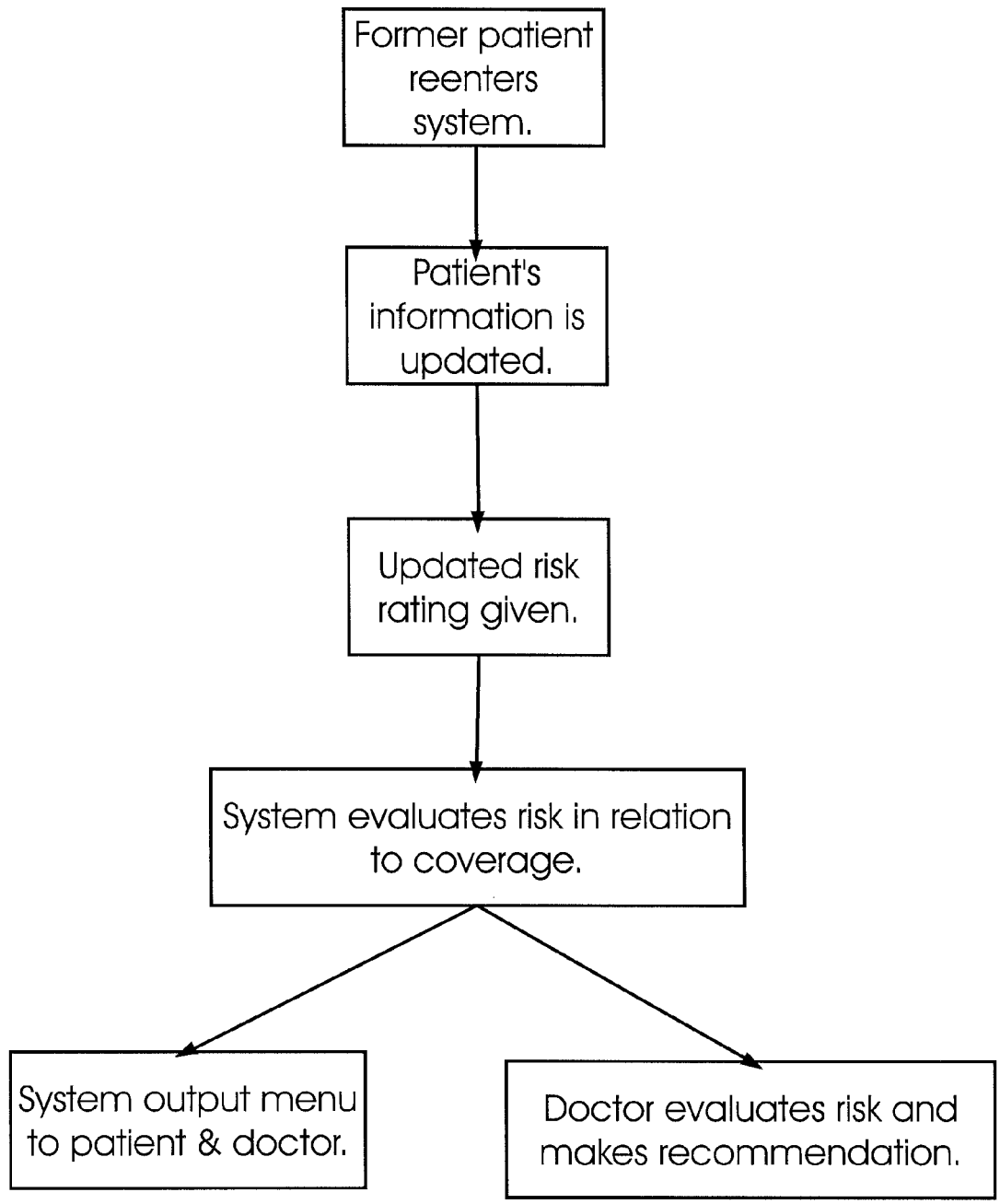
FIG. 18 is a flowchart summarizing the initial steps taken in the ninth preferred embodiment of the invention when an old patient reenters the system.

FIG. 18 illustrates the initial steps taken when an old or former patient reenters the system. The former patient may have been out of the Hygiea Health Care System for some time (and perhaps has gone to out-of-system providers). The patient's medical history and other information is updated and entered into the system. The patient is then given an updated risk rating. Hygiea's system then evaluates coverage in relation to risk and determines the cost of ranges of coverage based on the updated risk rating. The system prints out (or displays on a terminal) for the patient and doctor a menu of malpractice options and coverage. The doctor may also evaluate coverage in relation to risk and make a recommendation to the patient (perhaps to obtain more coverage).

Figure 19:
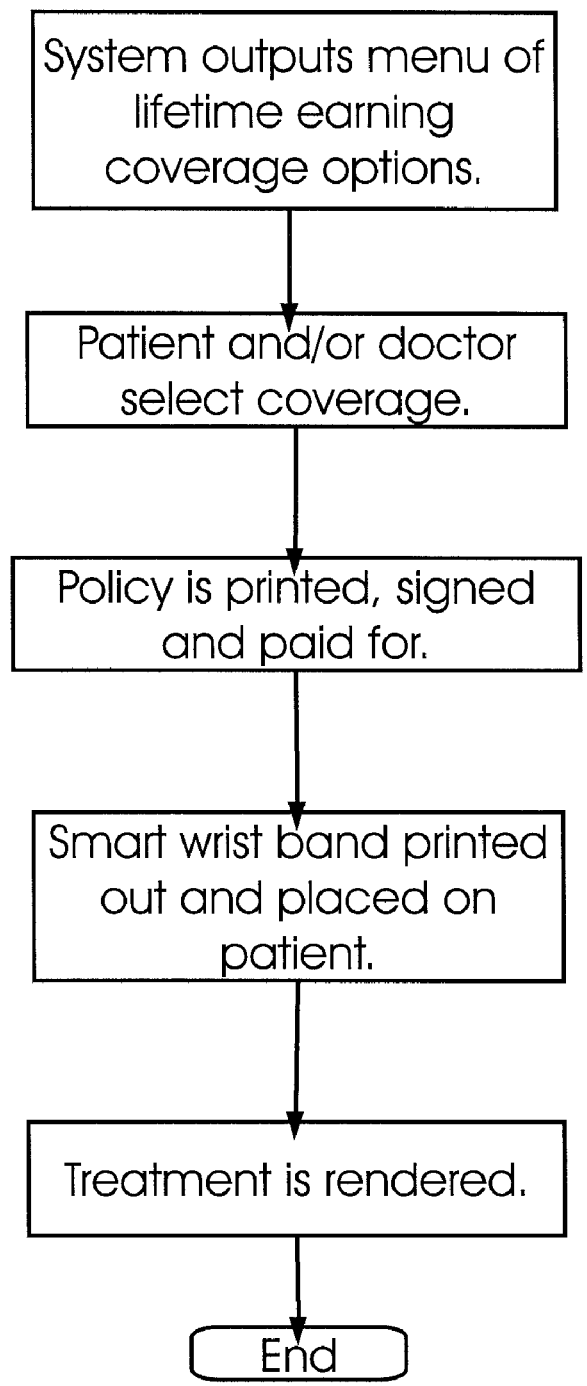
FIG. 19 is a flowchart summarizing the concluding steps taken in the ninth preferred embodiment of the invention when an old patient reenters the system.

FIG. 19 illustrates the concluding steps to be taken when an old patient has reentered the system. The system prints out (or displays on a terminal) a menu of lifetime earning coverage options for the patient and doctor to review. The patient and/or doctor select coverage. A policy is then printed, signed and paid for. A smart wrist band is printed out and placed on the patient. Treatment is then rendered.

Figure 20:
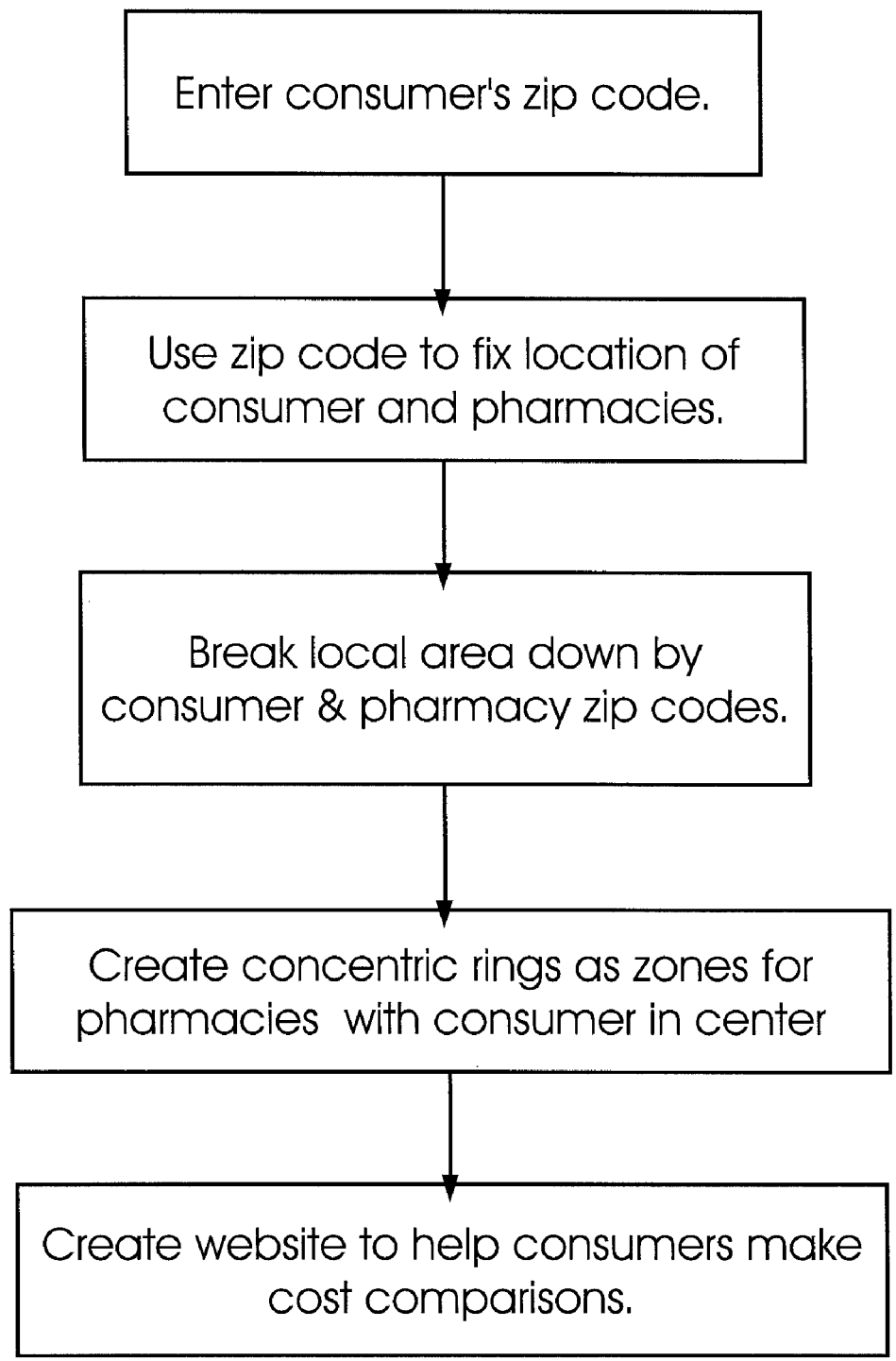
FIG. 20 is a flowchart summarizing the initial steps taken in the tenth preferred embodiment of the invention.

The tenth preferred embodiment is a method of drug cost analysis. FIG. 20 shown the initial steps in the method. The consumer's zip code is entered by the consumer or his health care provider. The zip code is used to determine the location of the consumer and nearby pharmacies. The local area is broken down by the zip codes of consumers and pharmacies. The consumer may be considered to be the bull's eye of a target, with concentric rings at fixed distances from the consumer demarcating zones within which pharmacies may be found. The price that a consumer is willing to pay for pharmaceuticals is assumed to be inversely related the distance of the pharmacies. A consumer may be willing to drive one mile to save a dollar, but may be willing to drive twenty miles to save one hundred dollars. Hygiea may provide a website to help consumers make cost comparisons.

Figure 21:
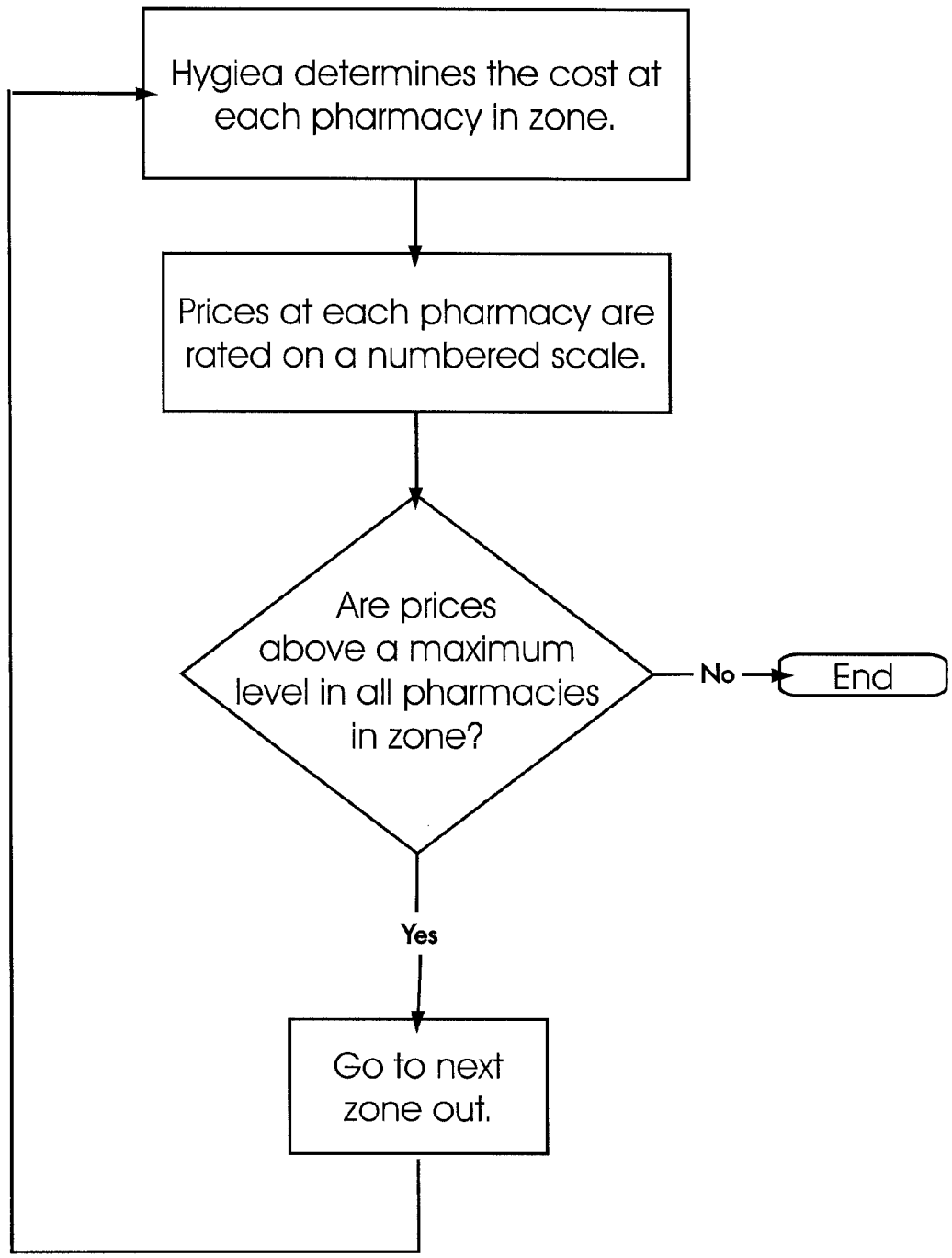
FIG. 21 is a flowchart summarizing further steps taken in the tenth preferred embodiment of the invention.

FIG. 21 illustrates further steps in the method. Hygiea determines the cost of filling prescriptions at each pharmacy in a defined area, so as to make "apple to apple" comparisons. Prices and locations are each rated on a numbered scale (e.g., 1 to 10). If a reasonable price cannot be found within an inner ring, Hygiea will analyze the next ring further out.

Figure 22:
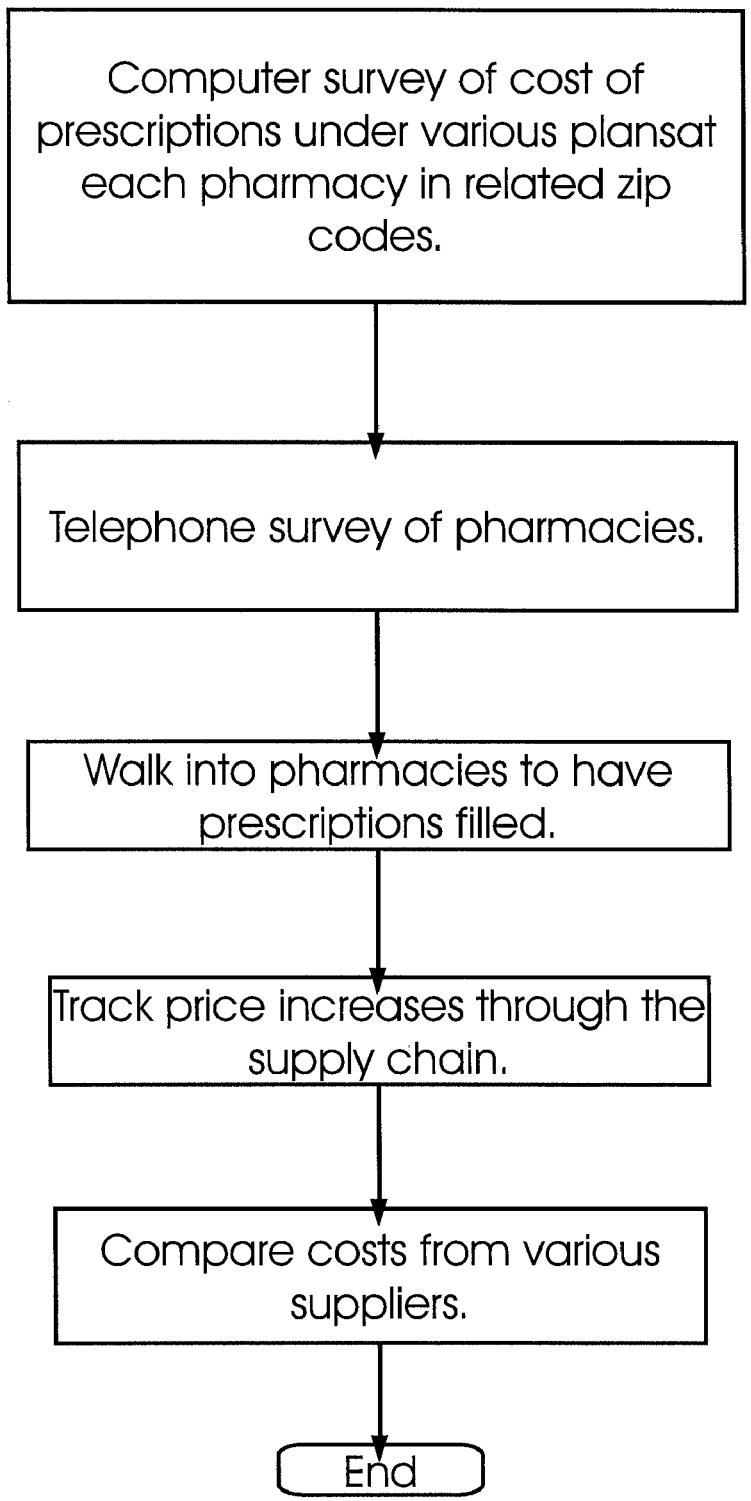
FIG. 22 is a flowchart summarizing concluding steps taken in the tenth preferred embodiment of the invention.

FIG. 22 illustrates concluding steps in the method. A computer survey of the cost of prescriptions under Medicare, Medicaid, Access, and other public or private health care plans is made at each pharmacy in related zip codes. Hygiea's staff perform a survey by telephone of pharmacies in the area. If necessary, the staff will go to the pharmacies to have prescriptions filled. They will track the increase in price through the drug supply chain from manufacturer to wholesaler to pharmacy to consumer. They will compare the costs to consumers of drugs from various suppliers, including pharmaceutical benefit management companies ("PBMs") and health maintenance organizations ("HMOs").

The eleventh preferred embodiment is a method of providing health care insurance to consumers on an individual basis as opposed to a group basis. The method uses objective criteria as well as actuarial information to determine the cost of a range of health insurance policies. A menu of choices, ranging from a simple to an extreme policy, with the cost of each, is provided to the individual. This enables the individual to pro-actively determine the type and cost of their health care insurance. The objective criteria include, but are not limited to, the individual consumer's age, occupation, weight, present and past medical history and health habits, codes for diseases suffered by the individual consumer (such as ICD-9 or ICD-10), and codes for procedures performed on the individual consumer (such as CPT). The premium for the policy is paid for by a medical or health savings account, an employer, the government (e.g., through Medicare, Medicaid or Access), or by another third party. But the individual would always be the beneficiary of the policy. The individual may use the services of a health care provider in making a selection from the menu, but is not required to do so. In addition to the policy selected from the menu, an additional catastrophic coverage plan is provided, which is paid for by the same party. The catastrophic coverage plan is a nominal cost plan (e.g., having a premium under fifty dollars) provided to all consumers and used for defined catastrophic needs only.

The eleventh preferred embodiment allows individuals, businesses and the government to pro-actively determine the cost of health insurance coverage on an individual as opposed to a group basis. The method cannot be used on a discriminatory basis, but can be used to isolate the small percentage of the population that uses the majority of health care resources, so that the government can design a system to care for this small percentage at a more reasonable and controlled cost. (As in the case of flood insurance, government will fill a need that cannot be met by private entities.)

It is to be understood that the present invention is not limited to the preferred embodiments described above, but encompasses any and all embodiments within the scope of the following claims.

I claim:

1. A risk rating method for a hospital, comprising the steps of:
   determining a risk rating for a designated hospital based on objective criteria, by determining the status of a plurality of objective criteria, assigning a point value to each objective criterion, based on its status, entering the point values into a computer, and determining the risk rating for the hospital from the point values using the computer;
   wherein the objective criteria are:
   the financial status of the hospital, with negative J points for each thousand dollars it is in debt;
   the income-generating ability of the hospital, with positive K points for each thousand dollars of annual profits, and negative K points for each thousand dollars of annual losses; and
   one or more criteria selected from a group comprising:
   the number of registered nurses per bed times A;
   the number of licensed practical nurses per bed times B;
   the number of medical specialists per bed times C;
   the number of medical subspecialists per bed times D;
   whether or not the hospital is a teaching hospital, with E points awarded if it is;
   the mean number of hours worked per week by medical residents, times F;

the mean number of hours worked per day by staff persons, times G;

the number of pharmacists per bed times H;

whether or not drug dispensing is automated, with I points awarded if it is;

whether or not nuclear medicine is practiced at the hospital, with L points awarded if it is;

the socioeconomic status of the area in which the hospital is located, determined by the difference between the mean income of the population residing within a radius of M miles from the hospital and the national mean income, times N per thousand dollars of annual income;

the time it takes to arrive at the hospital, determined by mean number of minutes that it takes emergency vehicles to arrive at the hospital from within a given radius, after a patient has entered the vehicle and it has been cleared to proceed to the hospital, divided by the distance in miles from the hospital, times P;

the types of insurance coverage that the hospital has, and the policy limits of each type, determined by the difference between the insurance premiums paid by the hospital and the national mean insurance premiums paid by hospitals with the same numbers of beds, times Q;

the backgrounds of the members of the hospital's governing board, determined by the mean number of years of college completed times R, and by the percentage who are United States citizens times S;

the number of physicians, interns, residents, nurses and other staff in the hospital's emergency room times T;

the number of types of infectious diseases treated at the hospital, times the number of patients having each type, times U;

the number of cardiology procedures done each year times V; and the number of other types of other medical procedures performed at the hospital, and the number of each type performed annually, times W wherein A through W are weighting factors, and the rating for the hospital is determined by adding J, K, and the point values for the criteria selected.

2. The risk rating method for a hospital according to claim 1, wherein the objective criteria are ten or more criteria selected from said group.

3. The risk rating method for a hospital according to claim 1, wherein the objective criteria are fifteen or more criteria selected from said group.

4. The risk rating method for a hospital according to claim 1, wherein the objective criteria are all of the criteria in said group.

5. The risk rating method for a hospital according to claim 1, wherein the objective criteria are five or more criteria selected from said group.

* * * * *